(12) United States Patent
Sweeney et al.

(10) Patent No.: US 8,521,276 B2
(45) Date of Patent: Aug. 27, 2013

(54) USE OF SIGNIFICANT POINT METHODOLOGY TO PREVENT INAPPROPRIATE THERAPY

(75) Inventors: Robert J. Sweeney, Woodbury, MN (US); Dan Li, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 146 days.

(21) Appl. No.: 13/004,582

(22) Filed: Jan. 11, 2011

(65) Prior Publication Data

US 2011/0172729 A1 Jul. 14, 2011

Related U.S. Application Data

(60) Provisional application No. 61/294,159, filed on Jan. 12, 2010.

(51) Int. Cl.
*A61N 1/00* (2006.01)
(52) U.S. Cl.
USPC ............... 607/5; 607/4; 607/7; 607/9; 607/14
(58) Field of Classification Search
USPC ............... 607/4, 5, 7, 14; 600/510, 509, 516, 600/517, 518, 521
See application file for complete search history.

(56) References Cited

U.S. PATENT DOCUMENTS

| | | | |
|---|---|---|---|
| 5,492,128 A | 2/1996 | Wickham | |
| 5,496,350 A | 3/1996 | Lu | |
| 5,558,098 A * | 9/1996 | Fain | ............................ 600/519 |
| 5,702,425 A | 12/1997 | Wickham | |
| 5,755,738 A | 5/1998 | Kim et al. | |
| 5,778,881 A | 7/1998 | Sun et al. | |
| 5,782,876 A | 7/1998 | Flammang | |
| 5,861,008 A | 1/1999 | Obel et al. | |
| 5,897,575 A | 4/1999 | Wickham | |

(Continued)

FOREIGN PATENT DOCUMENTS

| | | |
|---|---|---|
| WO | WO-02/40094 A2 | 5/2002 |
| WO | WO-2004/006763 A2 | 1/2004 |
| WO | WO-2011088043 A1 | 7/2011 |

OTHER PUBLICATIONS

Sweeney, Robert J, et al., "Significant point algorithm for tachyarrhythmia detection", Heart Rhythm, vol. 1(No. 1, Supp. 1), (May, 2004), S80.

(Continued)

*Primary Examiner* — Thomas J Sweet
*Assistant Examiner* — Krutanjali M Shah
(74) *Attorney, Agent, or Firm* — Schwegman Lundberg & Woessner, P.A.

(57) ABSTRACT

An apparatus example comprises a cardiac signal sensing circuit configured to provide a sensed cardiac signal representative of cardiac depolarization events of a subject, a sampling circuit coupled to the cardiac signal sensing circuit, a therapy circuit, and a controller communicatively coupled to the sampling circuit and the therapy circuit. The controller includes a detection module configured to detect tachyarrhythmia using the cardiac signal and a signal analysis module configured to establish significant points (SPs) of the sampled cardiac signal, estimate heart rate during the tachyarrhythmia using the SPs, and provide an indication of whether noise is present in the cardiac signal using the SPs. The controller is configured to select a therapy for delivery by the therapy circuit in response to the tachyarrhythmia detection and to modify the selected therapy according to the heart rate estimation and the noise indication.

18 Claims, 15 Drawing Sheets

(56) References Cited

U.S. PATENT DOCUMENTS

| | | | |
|---|---|---|---|
| 5,957,857 A | 9/1999 | Hartley | |
| 6,029,086 A | 2/2000 | Kim et al. | |
| 6,201,993 B1 | 3/2001 | Kruse et al. | |
| 6,223,078 B1 | 4/2001 | Marcovecchio | |
| 6,230,059 B1 | 5/2001 | Duffin | |
| 6,275,730 B1 * | 8/2001 | KenKnight et al. | 607/5 |
| 6,321,115 B1 * | 11/2001 | Mouchawar et al. | 607/9 |
| 6,381,494 B1 | 4/2002 | Gilkerson et al. | |
| 6,473,649 B1 | 10/2002 | Gryzwa et al. | |
| 6,490,478 B1 * | 12/2002 | Zhang et al. | 600/518 |
| 6,505,071 B1 | 1/2003 | Zhu et al. | |
| 6,597,942 B1 | 7/2003 | Yonce et al. | |
| 6,599,242 B1 | 7/2003 | Splett et al. | |
| 6,684,100 B1 | 1/2004 | Sweeney et al. | |
| 6,708,058 B2 | 3/2004 | Kim et al. | |
| 6,745,076 B2 | 6/2004 | Wohlgemuth et al. | |
| 6,754,527 B2 | 6/2004 | Stroebel et al. | |
| 6,839,587 B2 | 1/2005 | Yonce | |
| 6,862,476 B2 | 3/2005 | Mouchawar et al. | |
| 6,892,092 B2 | 5/2005 | Palreddy et al. | |
| 6,917,830 B2 | 7/2005 | Palreddy et al. | |
| 6,950,702 B2 | 9/2005 | Sweeney | |
| 6,985,768 B2 | 1/2006 | Hemming et al. | |
| 7,027,858 B2 | 4/2006 | Cao et al. | |
| 7,031,764 B2 | 4/2006 | Schwartz et al. | |
| 7,155,275 B2 | 12/2006 | Linder et al. | |
| 7,215,993 B2 | 5/2007 | Lin | |
| 7,248,921 B2 | 7/2007 | Palreddy et al. | |
| 7,289,845 B2 | 10/2007 | Sweeney et al. | |
| 7,330,757 B2 * | 2/2008 | Ostroff et al. | 607/5 |
| 7,467,009 B2 | 12/2008 | Palreddy et al. | |
| 7,477,932 B2 | 1/2009 | Lee et al. | |
| 7,500,955 B2 | 3/2009 | Sweeney | |
| 7,515,955 B2 | 4/2009 | Linder et al. | |
| 7,567,835 B2 | 7/2009 | Gunderson et al. | |
| 7,650,182 B2 | 1/2010 | Kim et al. | |
| 7,792,571 B2 | 9/2010 | Sweeney et al. | |
| 2003/0083713 A1 | 5/2003 | Palreddy | |
| 2005/0288600 A1 | 12/2005 | Zhang et al. | |
| 2006/0224075 A1 | 10/2006 | Gunderson et al. | |
| 2006/0247695 A1 | 11/2006 | Stalsberg et al. | |
| 2007/0038253 A1 * | 2/2007 | Kim et al. | 607/4 |
| 2007/0135722 A1 | 6/2007 | Lin | |
| 2007/0203419 A1 * | 8/2007 | Sweeney et al. | 600/510 |
| 2008/0161872 A1 | 7/2008 | Gunderson | |
| 2008/0172098 A1 | 7/2008 | Gunderson et al. | |
| 2008/0228093 A1 | 9/2008 | Dong et al. | |
| 2009/0093731 A1 | 4/2009 | Palreddy et al. | |
| 2009/0192395 A1 | 7/2009 | Sweeney | |
| 2009/0264716 A1 | 10/2009 | Shuros et al. | |
| 2010/0106209 A1 | 4/2010 | Gunderson et al. | |
| 2010/0204745 A1 | 8/2010 | Li et al. | |
| 2010/0305645 A1 | 12/2010 | Sweeney et al. | |
| 2012/0203123 A1 | 8/2012 | Mahajan et al. | |

OTHER PUBLICATIONS

"International Application Serial No. PCT/US2011/020834, International Search Report mailed May 4, 2011", 4 pgs.

"International Application Serial No. PCT/US2011/020834, Written Opinion mailed May 4, 2011", 9 pgs.

"International Application Serial No. PCT/US2011/020834, International Preliminary Report on Patentability mailed Jul. 26, 2012", 10 pgs.

Gunderson, Bruce D, et al., "Automatic Identification of Clinical Lead Dysfunctions", PACE, vol. 28, (Jan. 2005), S63-S67.

Rhude, Jennifer, et al., "New ICD Algorithm to Detect Lead Failure Noise and Prevent Inappropriate Therapy", Heart Rhythm, vol. 7, No. 5, PO5-127, (May 2010), S364-S365.

U.S. Appl. No. 13/357,085, filed Jan. 24, 2012, Noise Detection in Implantable Medical Devices.

* cited by examiner

USE OF SIGNIFICANT POINT METHODOLOGY TO PREVENT INAPPROPRIATE THERAPY

CROSS-REFERENCE TO RELATED APPLICATIONS

This application claims the benefit of U.S. Provisional Application No. 61/294,159, filed on Jan. 12, 2010, under 35 U.S.C. §119(e), which is incorporated herein by reference in its entirety.

BACKGROUND

Cardioverter defibrillators are medical devices that deliver an electrical shock to the heart via electrodes to terminate arrhythmias. The devices may use the same or a different set of electrodes to monitor electrical heart activity within a patient.

Automated external defibrillators (AEDs) include surface electrodes that are applied to a patient by a paramedic or other trained personnel. Wearable cardioverter defibrillators (WCDs) are personal external monitors that are worn by the patient and contain surface electrodes. The surface electrodes are arranged to provide one or both of monitoring surface electrocardiograms (ECGs) and delivering cardioverter and defibrillator shock therapy.

Implantable cardioverter defibrillators (ICDs) include implantable electrodes. The electrodes are connected to sense amplifiers to provide internal monitoring of a patient's condition. ICDs may include one or more sensors to monitor one or more other internal patient parameters. In other examples, the ICDs are included in a cardiac function management device (CFM) that provides a combination of device capabilities such as pacemaker therapy and cardiac resynchronization therapy (CRT).

Additionally, some medical devices detect events by monitoring electrical heart activity signals. These events can include heart chamber electrical depolarization and the subsequent expansions and contractions. By monitoring cardiac signals indicative of expansions or contractions, medical devices can detect abnormally rapid heart rate, such as tachyarrhythmia. Tachyarrhythmia includes ventricular tachycardia (VT) which originates from the ventricles. Tachyarrhythmia also includes rapid and irregular heart rate, or fibrillation, including ventricular fibrillation (VF). Abnormally rapid heart rate can also be due to supraventricular tachycardia (SVT). SVT is less dangerous to the patient than VT or VF. SVT includes arrhythmias such as atrial tachycardia, atrial flutter, and atrial fibrillation. A rapid heart rate can also be due to sinus tachycardia, which is a normal response to, for example, exercise or an elevated emotional state.

Typically, cardioverter defibrillators detect tachyarrhythmia by first detecting a rapid heart rate. When detected, ventricular tachyarrhythmia can be terminated using high-energy shock therapy. Other detection methods in addition to fast rate detection are used to reduce the incidence of inappropriate shocks. It is important for cardioverter defibrillators to quickly and accurately classify sensed rhythms or arrhythmias and deliver the appropriate therapy.

OVERVIEW

This document relates generally to systems, devices, and methods for providing therapy for device detected tachyarrhythmia. In example 1, an apparatus comprises a cardiac signal sensing circuit configured to provide a sensed cardiac signal representative of cardiac depolarization events of a subject, a sampling circuit coupled to the cardiac signal sensing circuit, a therapy circuit, and a controller communicatively coupled to the sampling circuit and the therapy circuit. The therapy circuit is configured to provide one or more of high-energy cardioversion shock therapy, high-energy defibrillation shock therapy, and anti-tachycardia pacing to the heart. The controller includes a detection module configured to detect tachyarrhythmia using the cardiac signal and a signal analysis module configured to establish significant points (SPs) of the sampled cardiac signal that corresponds to a time of occurrence of a turn encountered in the cardiac signal. The signal analysis module also estimates heart rate during the tachyarrhythmia using the SPs and provides an indication of whether noise is present in the cardiac signal using the SPs. The controller is configured to select a therapy for delivery by the therapy circuit in response to the tachyarrhythmia detection and to modify the selected therapy according to the heart rate estimation and the noise indication.

In example 2, the signal analysis module of example 1 is optionally configured to determine a probability of noise in the cardiac signal using the SPs.

In example 3, the signal analysis module of example 2 is optionally configured to identify a number of approximate SP pairs in the cardiac signal, calculate the probability of noise in the cardiac signal using the number of approximate SP pairs, and provide the indication of noise according to the calculated noise probability.

In example 4, the signal analysis module of any of examples 2 or 3 is optionally configured to determine a number of SPs per second in the cardiac signal, calculate the probability of noise in the cardiac signal using the number of SPs per second, and provide the indication of noise according to the calculated noise probability.

In example 5, the signal analysis module of any one of examples 1-4 is optionally configured to perform autocorrelation of the SPs in an SP domain, filter the SP autocorrelation, calculate a number of SPs per heart beat from an SP shift that produces a peak in the filtered autocorrelation, and estimate heart rate using the number of SPs per heart beat.

In example 6, the signal analysis module of any one of examples 1-4 is optionally configured to perform autocorrelation of the SPs in an SP domain, perform a second autocorrelation of the SP autocorrelation, calculate a number of SPs per heart beat from an SP shift that produces a peak in the second autocorrelation, and estimate heart rate using the number of SPs per heart beat.

In example 7, the controller of any one of examples 1-6 is optionally configured to change a selected therapy type to a less aggressive therapy type when the estimated heart rate is within a lowest tachyarrhythmia detection rate zone and the noise assessment indicates that a probability of noise is above a noise probability threshold value.

In example 8, the controller of any one of examples 1-7 is optionally configured to withhold delivery of the selected therapy when the noise assessment indicates that a probability of noise is above a noise probability threshold value and the estimated heart rate is lower than the lowest tachyarrhythmia detection rate zone.

In example 9, the detection module of any of examples 1-8 is optionally configured to detect tachyarrhythmia when heart rate determined from heart beats sensed in the cardiac signal exceeds a tachyarrhythmia detection rate threshold or interval threshold, and the controller of the examples is optionally configured to withhold delivery of the selected therapy when the noise assessment indicates that a probability of noise is above a noise probability threshold value and the estimated rate using the SPs differs from the heart rate determined from the sensed cardiac signal by more than a threshold difference value.

In example 10, the detection module of any one of examples 1-8 is optionally configured to detect tachyarrhythmia when heart rate determined from heart beats sensed in the cardiac signal exceeds a tachyarrhythmia detection rate threshold or interval threshold, and the controller of any one of examples 1-9 is optionally configured to deliver a type of therapy less aggressive than the selected therapy when the noise assessment indicates that a probability of noise is above a noise probability threshold value, and the heart rate estimated using the SPs is within or below the lowest tachyarrhythmia detection rate zone.

In example 11, a method includes sampling a sensed cardiac signal using a medical device that delivers at least one of high-energy cardioversion, high-energy defibrillation shock therapy, or anti-tachycardia pacing (ATP), and detecting tachyarrhythmia using the cardiac signal. In response to the tachyarrhythmia detection the method includes selecting a therapy for delivery by the medical device, establishing significant points (SPs) of the sampled cardiac signal, wherein an SP corresponds to a turn encountered in the cardiac signal, estimating heart rate during the tachyarrhythmia using the SPs, assessing whether noise is present in the cardiac signal using the SPs, and modifying the selected therapy according to the rate estimation and the noise assessment.

In example 12, the assessing whether noise is present of example 1 optionally includes determining a probability of noise in the cardiac signal using the SPs.

In example 13, the determining a probability of noise of example 12 optionally includes identifying a number of approximate SP pairs in the cardiac signal and calculating the probability of noise in the cardiac signal using the number of approximate SP pairs.

In example 14, the determining a probability of noise of example 12 or 13 optionally includes calculating the probability of noise in the cardiac signal using a number of SPs per second in the cardiac signal.

In example 15, the estimating heart rate of any one of examples 11-14 optionally includes performing autocorrelation in an SP domain, filtering the SP autocorrelation, and calculating a number of SPs per heart beat from an SP shift that produces a peak in the filtered autocorrelation.

In example 16, the estimating heart rate of any one of examples 11-14 optionally includes performing autocorrelation in an SP domain, performing a second autocorrelation of the SP autocorrelation, and calculating a number of SPs per heart beat from an SP shift that produces a peak in the second autocorrelation.

In example 17, the modifying the selected therapy of any one of examples 11-16 optionally includes changing a selected therapy type to a less aggressive therapy type when the estimated heart rate is within a lowest tachyarrhythmia detection rate zone and the noise assessment indicates that a probability of noise is above a noise probability threshold value.

In example 18, the modifying the selected therapy of any one of examples 11-17 optionally includes withholding delivery of the selected therapy when the noise assessment indicates that a probability of noise is above a noise probability threshold value and the estimated heart rate is lower than the lowest tachyarrhythmia detection rate zone.

In example 19, the detecting tachyarrhythmia using the cardiac signal of any one of claim 11-18 optionally includes detecting tachyarrhythmia when heart rate determined from the sensed cardiac signal exceeds a tachyarrhythmia detection rate threshold or interval threshold, and the modifying the selected therapy of the examples optionally includes withholding delivery of the selected therapy when the noise assessment indicates that a probability of noise is above a noise probability threshold value and the estimated heart rate using the SPs differs from the rate determined from the sensed cardiac signal by more than a threshold difference value.

In example 20, the detecting tachyarrhythmia using the cardiac signal of any one of claim 11-18 optionally includes detecting tachyarrhythmia when heart rate determined from the cardiac signal exceeds a tachyarrhythmia detection rate threshold or interval threshold, and the modifying the selected therapy of any one of examples 11-19 optionally includes withholding delivery of the selected therapy when the noise assessment indicates that a probability of noise is above a noise probability threshold value, the heart rate estimated using the SPs differs from the heart rate determined from the sensed cardiac signal by less than a threshold difference value, and the heart rate estimated using the SPs is less than the lowest tachyarrhythmia detection rate threshold.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

A medical device may include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable, partially implantable, or wearable device need not include all of the features described herein, but may be implemented to include selected features that provide for unique structures or functionality. Such a device may be implemented to provide a variety of therapeutic or diagnostic functions.

This document discusses, among other things, systems, devices, and methods for detecting tachyarrhythmia. When VT is detected, medical devices are designed to provide therapy to the patient. Cardioverter defibrillators treat VT by delivering a high energy electrical shock to the heart. Another therapy for tachyarrhythmia is anti-tachycardia pacing (ATP). ATP may be delivered by an implantable or partially implantable pacemaker or by an ICD. ATP uses lower energy pacing energy to establish a regular rhythm in a heart. This allows the tachycardia to be converted to a normal heart rhythm without exposing the patient to high energy defibrillation therapy that can be painful to the patient. Providing painless therapy, such as ATP therapy, improves the patient's experience with an IMD as well as increasing the battery longevity of the devices.

Some types of tachyarrhythmia considered to be serious enough to warrant delivering shock therapy immediately, such as VF or a VT with a fast heart rate (i.e., fast VT). Other types of tachyarrhythmia may be considered less urgent (e.g., slow VT, or SVT) and a medical device may be configured to first try to convert the tachyarrhythmia using a less aggressive therapy such as ATP. For some arrhythmias (e.g., SVT) a medical device may be programmed to not provide any therapy.

If a medical device incorrectly interprets a detected arrhythmia, the device may inappropriately deliver shock therapy or other therapy. Typically, the majority of inappropriate shocks are delivered when a device fails to correctly distinguish a heart arrhythmia as being SVT. For those inappropriate shocks delivered to rhythms that are not SVT, five to eleven percent of the inappropriate shocks are delivered due to noise or over-sensing by cardiac sense amplifiers. Even this percentage has a disproportionately high negative impact on the perception of the device by the patients and clinicians. Additionally, because an underlying rhythm is not responsible for the inappropriate shock therapy delivery in this case, there is not an arrhythmia to convert and inappropriate shocks may continue to be delivered as long as noise is present or until the ability to deliver therapy is exhausted. Thus, it is desirable for a medical device to correctly recognize and prevent inappropriate delivery of shock therapy.

Figure 1:
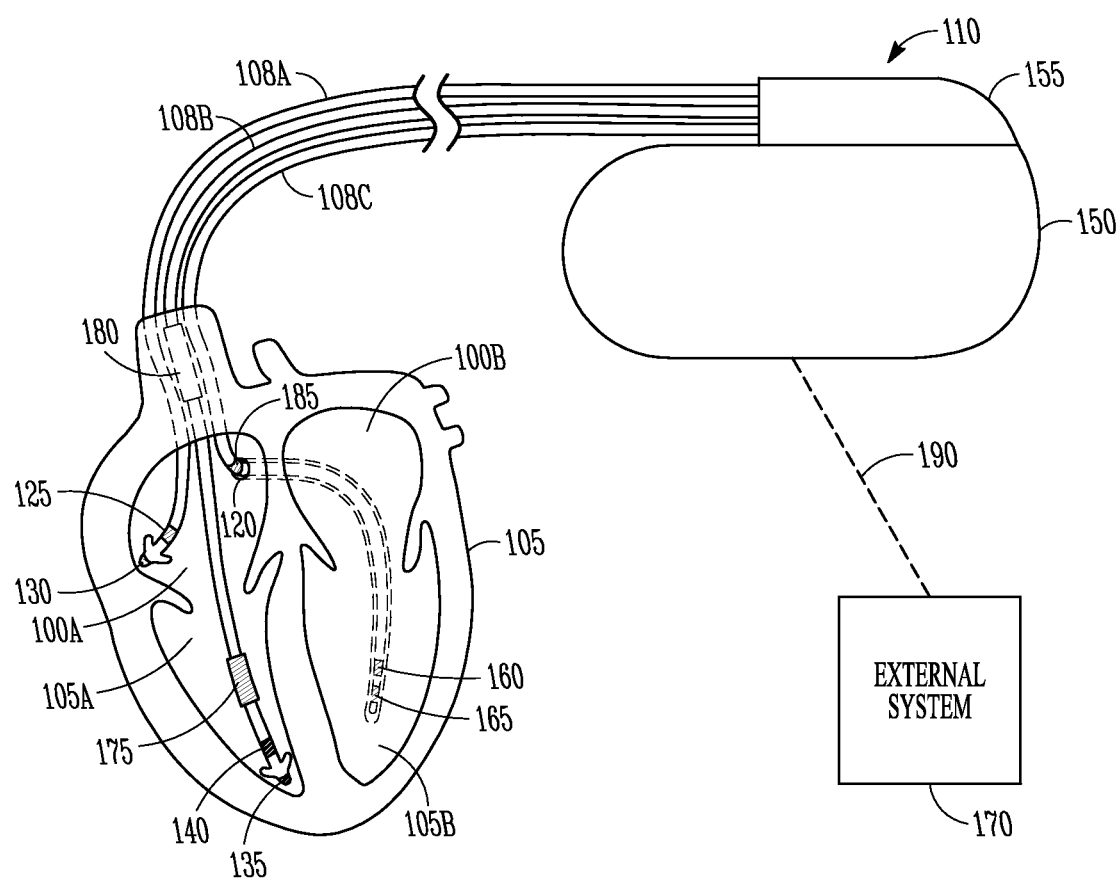
FIG. 1 is an illustration of portions of a system that uses an implantable medical device.

FIG. 1 is an illustration of portions of a system that uses an implantable medical device (IMD) 110. Examples of IMD 110 include, without limitation, a cardioverter defibrillator, a pacer, a cardiac resynchronization therapy (CRT) device, or a combination of such devices. The system also typically includes an IMD programmer or other external device 170 that communicates wireless signals 190 with the IMD 110, such as by using radio frequency (RF) or other telemetry signals.

The IMD 110 is coupled by one or more leads 108A-C to heart 110. Cardiac leads 108A-C include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies, voltages, and currents involved in defibrillation. Lead 108B optionally provides resynchronization therapy to the heart 105. Resynchronization therapy is typically delivered to the ventricles in order to better synchronize the timing of depolarizations between ventricles.

The IMD 110 may include a third cardiac lead 108C attached to the IMD 110 through the header 155. The third cardiac lead 108C includes ring electrodes 160 and 165 placed in a coronary vein lying epicardially on the left ventricle (LV) 105B via the coronary vein. The third cardiac lead 108C may include a ring electrode 185 positioned near the coronary sinus (CS) 120.

Lead 108B may include a first defibrillation coil electrode 175 located proximal to tip and ring electrodes 135, 140 for placement in a right ventricle, and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to an electrode formed on the hermetically-sealed IMD housing or can 150. This improves defibrillation by delivering current from the RV coil 175 more uniformly over the ventricular myocardium. In some examples, the therapy is delivered from the RV coil 175 only to the electrode formed on the IMD can 150.

Note that although a specific arrangement of leads and electrodes are shown the illustration, the present methods and systems will work in a variety of configurations and with a variety of electrodes. Other forms of electrodes include meshes and patches which may be applied to portions of heart 105 or which may be implanted in other areas of the body to help "steer" electrical currents produced by IMD 110. The IMDs may be configured with a variety of electrode arrangements, including transveous, endocardial, or epicardial electrodes (e.g., intrathoracic electrodes), or subcutaneous, non-intrathoracic electrodes, such as can, header, or indifferent electrodes, or subcutaneous array or lead electrodes (e.g., non-intrathoracic electrodes). WCDs and AEDs may contain surface electrode arrangements for one or both of monitoring surface electrocardiograms (ECGs) and delivering cardioverter and defibrillator shock therapy. Monitoring of electrical signals related to cardiac activity may provide early, if not immediate, diagnosis of cardiac disease.

Some medical devices may include a sampling circuit to sample a cardiac signal. A sampling circuit may include an analog to digital converter (ADC) to convert a sensed cardiac signal to discrete digital values.

Curvature Based Analysis

For a voltage versus time cardiac signal, characteristics of a sensed cardiac signal can be analyzed in terms of those points along the signal where it makes significant "turns." Characterizing these significant turns in the signal provides additional information useful for correctly categorizing sensed cardiac signals.

Figure 2:
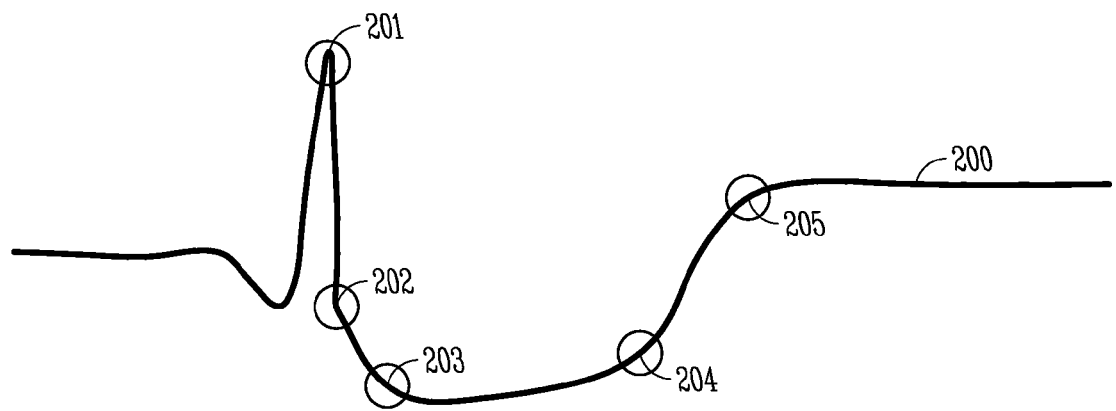
FIG. 2 illustrates an artificial representation of an electrogram signal.

In general, these characteristic points or significant points (SPs) corresponding to the signal turns are different from those that would be selected using first or second derivative criteria. FIG. 2 illustrates a representation of an electrogram 200. An electrogram or egram is a sampled cardiac signal that is sensed using implantable electrodes such as those described previously herein. Electrograms may be sensed using electrodes to deliver electrical pacing therapy, which is sometimes called a rate channel (e.g., electrodes 140 and 135 in FIG. 1). Electrograms may also be sensed using electrodes to deliver higher energy shock therapy such as cardioversion or defibrillation shock therapy, which is sometimes called a shock channel (e.g., electrode 190 and an electrode formed on IMD can 150).

In FIG. 2, the R wave, denoted as point 201, has a high second derivative $d^2V/dt^2$. The electrogram sections on either side of point 201 have high positive and negative slopes detectable using a first derivative criterion. However, those points with these large (or even maximum) slopes do not convey any particularly significant description of the electrogram. For example, at each time along a segment between points 201 and 202, the waveform has a large negative slope but no point along this segment stands out significantly from any other.

On the other hand, points 202, 203, 204 and 205 are neither maximums nor minimums of the electrogram or its derivatives. These points are descriptive of the arbitrary waveform shape. Points 202, 203, 204 and 205 are significant because they mark locations where the signal makes significant turns. The turn at point 201 is very sharp and the turns at points 203 and 205 are less sharp turns and more broad. The turns at points 202 and 204 are even less sharp. The present subject matter detects SPs such as 201, 202, 203, 204 and 205 using a criteria based on the curvature of the signal.

Figure 3:
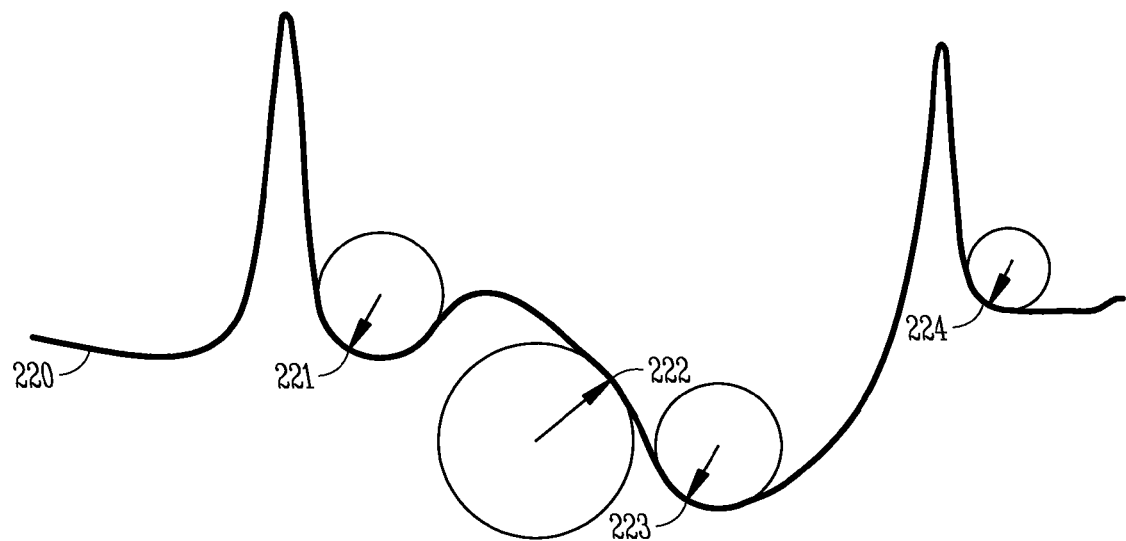
FIG. 3 illustrates curvature in a signal or waveform.

According to some examples of the present subject matter, signal curvature is illustrated in FIG. 3. An example of an electrogram 220 is shown in the Figure. At each point along electrogram 220, an osculating circle can be found that fits tangentially with the local portion of the electrogram. Each circle has a radius. The curvature of electrogram 220 at that point is the inverse of that radius so that small circles have large curvatures while large circles have small curvature. FIG. 3 shows these circles at selected points. At point 222, the circle is larger, and thus the curvature is smaller, than at points 221, 223 and 224. At points 221, 223 and 224, the turns are sharper and the curvature is larger.

In general, the curvature at point (X, Y) of an arbitrary curve in a two-dimensional space is expressed as:

$$\text{Curvature} = \frac{d^2Y/dX^2}{[1+\{dY/dX\}^2]^{3/2}}.$$

As seen, the curvature is a non-linear combination of both the first and second derivatives of the curve. At those points along the curve where the first derivative is zero (for example, point 201 in FIG. 2), the curvature is equal to the second derivative and at points where the second derivative is zero (for example, any straight section regardless of its slope), the curvature is zero.

The present subject matter calculates curvature of a sensed cardiac signal on a sample-by-sample basis. To determine dimensionality of curvature, consider curvature as a waveform where both the X axis and Y axis have the same dimensions (say time); then curvature has a dimension of 1/time. For a cardiac signal having a voltage as a function of time V(t), such as an electrogram or electrocardiogram, the signal is transformed into a time-versus-time signal T(t) according to T(t)=V(t)/U where U is a constant with dimensions of voltage/time. With this transformation, the first and second derivatives of T(t) become $$\frac{dT}{dt}(t) = \frac{dV}{dt}(t) \cdot 1/U$$

which is dimensionless and $$\frac{d^2T}{dt^2}(t) = \frac{d^2V}{dt^2}(t) \cdot 1/U$$

which has dimensions of 1/time and thus the curvature has dimensions of 1/time. Curvature is then expressed as:

$$\text{Curvature} = \frac{d^2T(t)/dt^2}{[1+\{dT(t)/dt\}^2]^{3/2}} = \frac{d^2V(t)/dt^2/U}{[1+\{dV(t)/dt/U\}^2]^{3/2}}$$

which has dimensions of 1/time and U has a numerical value.

Next consider curvature as a function of signal gain or amplitude of the input signal. Assume arbitrary dimensionless gain G is applied to the input signal to find a new input signal F(t) wherein F(t)=G·T(t)=V(t)·G/U. The curvature of the gained signal is then:

$$\text{Curvature} = \frac{d^2 F(t)/dt^2}{[1+\{dF(t)/dt\}^2]^{3/2}} = \frac{d^2 V(t)/dt^2 \cdot G/U}{[1+\{dV(t)/dt \cdot G/U\}^2]^{3/2}}.$$

The ratio G/U can be expressed as W having dimensions of time/voltage. For instance, the input signal can be a voltage sampled with a 12-bit analog-to-digital converter (ADC) having numerical voltage values in the range +/−2048 where each value represents a number of basic amplitude units ΔV, or voltage resolution. In certain examples, the amplifiers in the present subject matter are adjusted so that the samples from V(t) largely fill this range. Further, it is assumed that the samples are taken at a fixed rate and thus the time is represented by an integer number of samples with each sample representing a time interval ΔT=time resolution=1/(sample rate).

Figure 4:
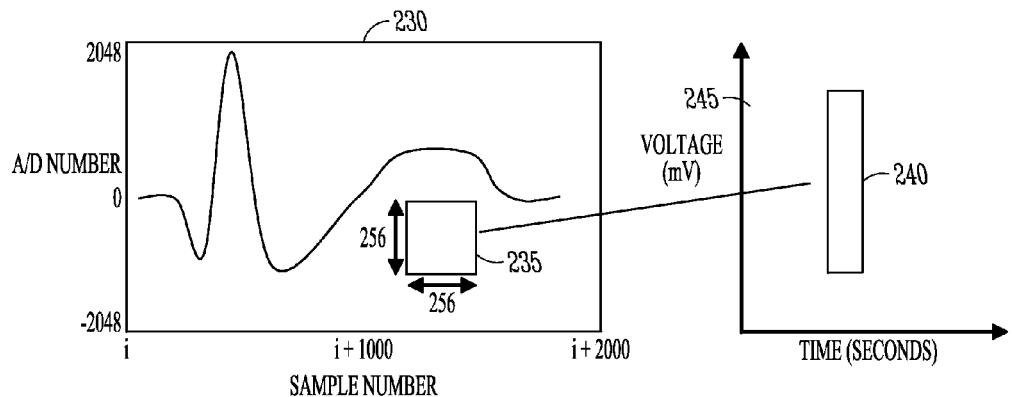
FIG. 4 illustrates a sampled signal in X-Y space having sample numbers on the X-axis and the analog-to-digital conversion value of the sample on the Y-axis.

FIG. 4 illustrates numerical X-Y space 230 which is denoted by sample numbers on the X-axis and the analog-to-digital conversion value on the Y-axis. Consider square 235 in X-Y space 230 which is 256 steps along the X-axis and 256 steps along the Y-axis and rectangle 240 in voltage-time space 245 that this square represents. Rectangle 240 has a width of 256/(sample rate), in seconds and a height of 256/(voltage resolution), in volts. Depending on the values selected for ΔV and ΔT, this rectangle may or may not be a square in voltage-time space.

In certain examples, W is selected to require that a square in voltage-time space be represented by a square in sample-sample space. Under that condition, the curvature versus time relationship that exists in voltage-time space is preserved in sample-sample space.

Figure 5:
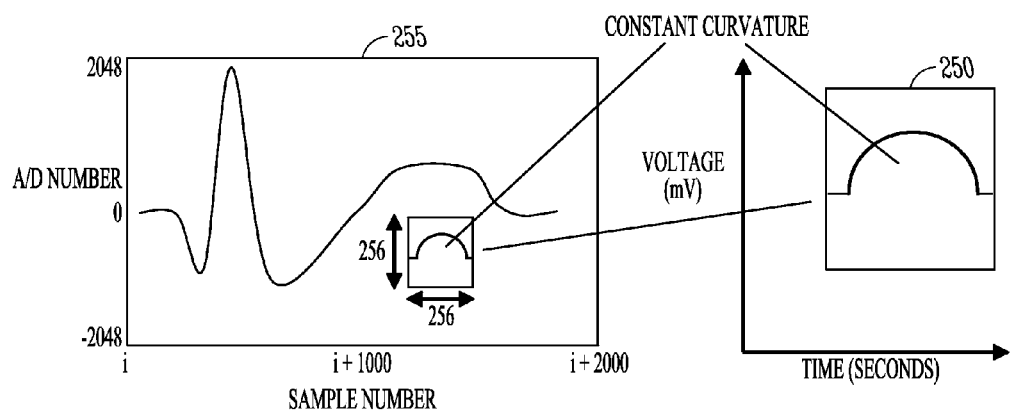
FIG. 5 shows an artificial voltage-time curve that forms a semicircle.

FIG. 5 shows an artificial voltage-time curve that forms a semicircle inside square box 250. Traversing from left to right across box 250 in voltage time space, the curvature of the signal is zero until the semicircle is encountered. The curvature jumps to a constant value, equal to 1/radius of the circle, and again jumps to zero at the end of the semicircle. For a particular value of W, the representation of this signal in sample-sample space 255 also has a constant curvature and for other values of W, the curvature would not be constant in sample-sample space.

To maintain this relationship between voltage-time and sample-sample space, W is selected as follows. In voltage-time space, the box T wide by V high is taken to be square. In sample-sample space, the box is T/ΔT time-samples wide and GV/ΔV voltage-samples high and through a transformation, the voltage sample is converted into time-samples using U so that the sample-space square has dimensions of T/ΔT by VG/ΔV/U. For the box to be square in sample-space, and assuming the box (V by T) in voltage-time space is square, then (V/ΔV)·G/U=T/ΔT or G/U=W=(T/ΔT)/(V/ΔV).

According to some examples, curvature is based on the first and second derivative of the signal. A least square cubic polynomial fit is used to reduce the noise that would otherwise result from using numerical estimates for the derivatives and using non-linear calculations to find curvature.

The sampled voltage signal is expressed as V(t)=V(I·ΔT) where t=i·ΔT so that the fit of size N uses 2N+1 voltage samples centered on the time t, thus:

V([i−n]·ΔT), . . . V([i−2]·ΔT),V([i−1]·ΔT),V(i·ΔT),V([i+1]·ΔT),V([i+2]·ΔT), . . . V([i+n]·ΔT).

This set of 2N+1 sampled data points is used to make the least-squares cubic fit which is given as $V_{est}[i \cdot \Delta T + dt] = A_i + B_i \cdot [dt] + C_i \cdot [dt]^2 + D_i \cdot [dt]^3$ where Ai, Bi, Ci, and Di are coefficients determined by minimizing the square error for the fit and dt represents a time step away from i·ΔT at which $V_{est}$ is evaluated. The coefficients in the polynomial are denoted with an i to indicate that they are valid for the point i ΔT.

Using the above equations, the curvature on a point to point basis, at the time i·ΔT, becomes $$\text{Curvature}(i \cdot \Delta T) = \frac{d^2 V(t)/dt^2 \cdot W}{[1+\{dV(t)/dt \cdot W\}^2]^{3/2}} = \frac{2 \cdot C_i \cdot W}{[1+\{B_i \cdot W\}^2]^{3/2}}.$$

Sample points, however, will not necessarily fall at the times where the signal curvature has a maximum or minimum value. Thus, sometimes the curvature signal is integrated between adjacent sample points using estimates for the first and second derivative of the signal at the sample points.

Further simplification yields an expression for average point curvature as:

$$Cavg_i = \frac{1}{(B_i - B_{i-1})^2} \cdot \left\{ \frac{C_{i-1} \cdot B_i^2 - C_i \cdot B_i \cdot B_{i-1} - C_i + C_{i-1}}{(B_i^2 + 1)^{1/2}} + \frac{C_i \cdot B_{i-1}^2 - C_{i-1} \cdot B_{i-1} \cdot B_i + C_i - C_{i-1}}{(B_{i-1}^2 + 1)^{1/2}} \right\}, B_i \neq B_{i-1}$$

$$Cavg_i = \frac{1}{2} \cdot \frac{C_i + C_{i-1}}{(B_i^2 + 1)^{3/2}}, B_i = B_{i-1}$$

As noted, curvature is computed on a sample-by-sample basis from the input signal.

Figure 6:
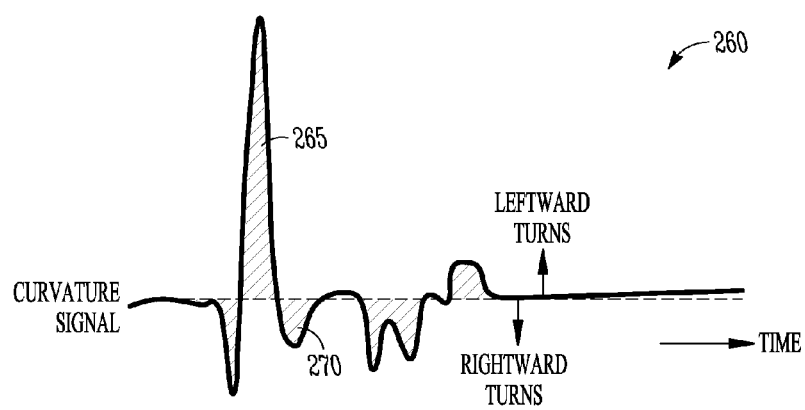
FIG. 6 is an artificial waveform showing curvature.

SPs in the signal correspond to turns in the signal. Turns in the original signal are reflected as excursions above and below zero in the curvature signal. As suggested by curvature in the waveform 260 of FIG. 6, each lobe above zero (for example, lobe 265) or below zero (for example, lobe 270) then represents a single turn in the input signal. Curvature lobes of opposite directions reflect opposite turns (leftward or rightward) in the signal. The area under each lobe reflects the total angle included in the turn. A point-by-point method is used to identify the lobes as they occur and to find the area and centroid of each lobe.

Curvature values are generated on a sample by sample basis. At each sample time, CRV represents the current curvature value and $CRV_{old}$ represents the previous value that is retained from the previous sample. When the curvature value is zero, the original signal is not turning so that no SPs may exist. The value CRV will rarely be exactly equal to zero.

In some examples, a dead-zone surrounding zero is defined where the calculated curvature may be treated as equal to zero. For times where the curvature is within the zone, the signal is not turning significantly. The zone is defined with a curvature threshold value and extends above and below zero from $+CRV_{thresh}$ to $-CRV_{thresh}$.

In certain examples, nine cases are identified for considering the value of CRV relative to the threshold and the absence or direction of a lobe. These cases can be described as follows:

Case 1: $CRV > CRV_{thresh}$ and not in a lobe.

Here, the current curvature value is above the dead-zone and the curvature signal is not currently in a lobe. Thus, a positive lobe has just started so the positive lobe initialization calculations will follow.

Case 2: $CRV_{thresh} \geq CRV \geq -CRV_{thresh}$ and not in a lobe.

Here, the current curvature values are inside the dead-zone and the curvature signal is not currently in a lobe.

Case 3: $CRV < -CRV_{thresh}$ and not in a lobe.

Here, the current curvature value is below the dead-zone and the curvature signal is not currently in a lobe. Thus, a negative lobe has just started so the negative lobe initialization calculations will follow.

Case 4: $CRV > CRV_{thresh}$ and in a positive lobe.

Here, the current curvature value is above the dead-zone and the curvature signal is in a positive lobe. Thus, the positive lobe continuation calculations will follow.

Case 5: $CRV_{thresh} \geq CRV \geq -CRV_{thresh}$ and in a positive lobe.

Here, the current curvature value is inside the dead-zone and the curvature signal is in a positive lobe. Thus, a positive lobe has just ended so the positive lobe finalization calculations will follow.

Case 6: $CRV < -CRV_{thresh}$ and in a positive lobe.

Here, the current curvature value is below the dead-zone and the curvature signal is currently in a positive lobe. Thus, a positive lobe has just ended and a negative lobe has just started so that both the positive lobe finalization calculations and the negative lobe initialization calculations will follow.

Case 7: $CRV > CRV_{thresh}$ and in a negative lobe.

Here, the current curvature value is above the dead-zone and the curvature signal is in a negative lobe. Thus, a negative lobe has just ended and a positive lobe has just started so that both the negative lobe finalization calculations and the positive lobe initialization calculations will follow.

Case 8: $CRV_{thresh} \geq CRV \geq -CRV_{thresh}$ and in a negative lobe.

Here, the current curvature value is inside the dead-zone and the curvature signal is in a negative lobe. Thus, a lobe has just ended so the negative lobe finalization calculations will follow.

Case 9: $CRV < -CRV_{thresh}$ and in a negative lobe.

Here, the current curvature value is below the dead-zone and the curvature signal is in a negative lobe. Thus, the negative lobe continuation calculations will follow.

In certain examples, hysteresis is used to aid in identifying curvature lobes. After having started a lobe, the curvature value crosses a threshold value closer to zero in order for the lobe to finish. Thus, hysteresis introduces another threshold value.

Once a lobe is identified, the lobe can be characterized by such measurements as the total area of the lobe, the time of the lobe area centroid and the value of the original data at the time of the area centroid. In certain examples, other measurements are used, including, for example, the peak curvature in the lobe, the time of the peak curvature, and the times of the lobe start and lobe finish.

Figure 7:
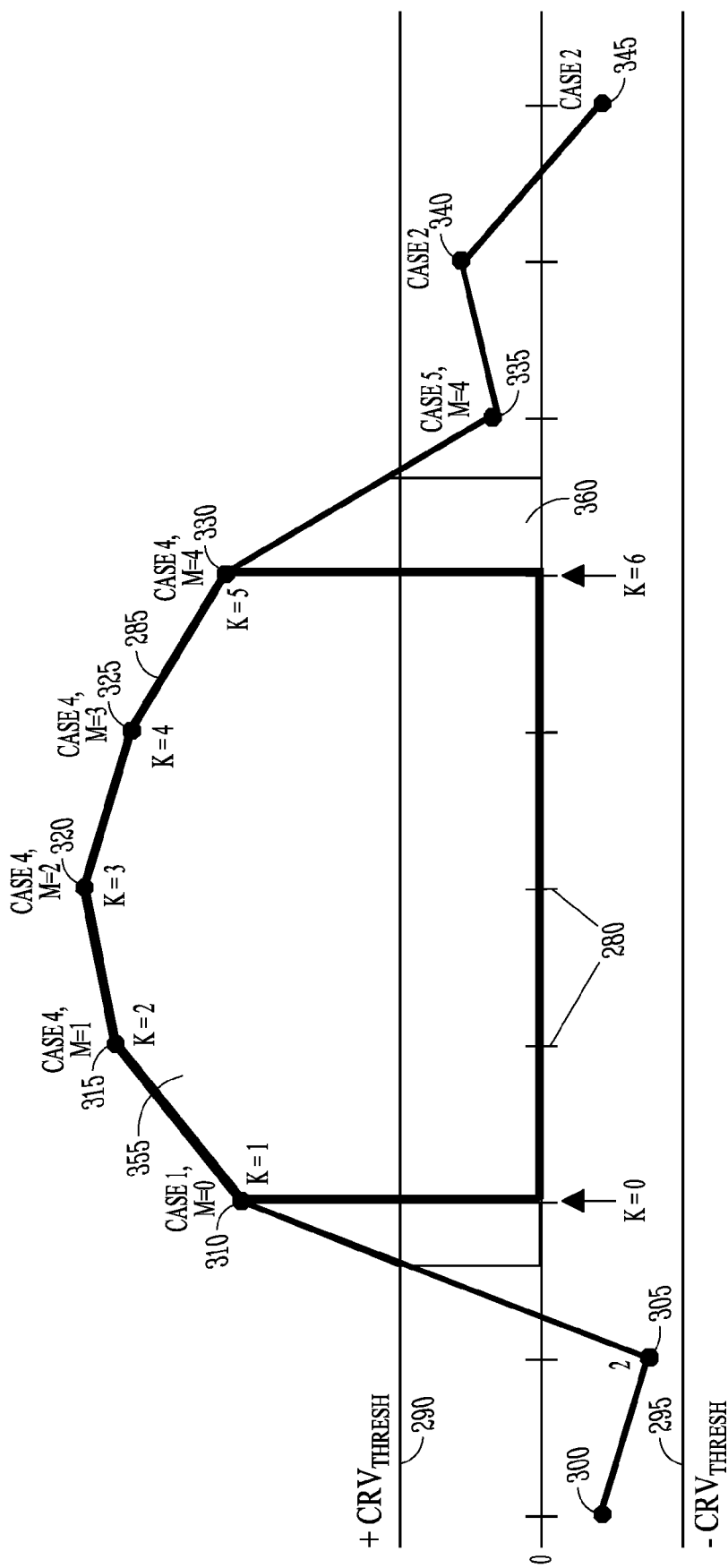
FIG. 7 shows an example of a curvature lobe of a sampled signal segment.

FIG. 7 shows an example of curvature lobe 285 as a series of calculated curvatures at each sample time. Tick marks 280 along the X axis represent the signal samples and thus are separated by $\Delta T$. Zero curvature is shown as the X axis. The threshold curvature values, $+CRV_{thresh}$ 290 and $-CRV_{thresh}$ 295 are shown as horizontal lines above and below the X-axis. Curvature points 300-345 are shown as dots.

As shown in the figure, initial curvature values at curvature points 300 and 305 are within the dead-zone of the threshold curvature values and thus, no lobe is yet established. Curvature point 310 is above the threshold and corresponds to Case 1 described above. The magnitude of initial area 350 is calculated as soon as the lobe is started according to case 1 described above. Upon determining curvature point 315, a contribution to the magnitude of main area 355 is calculated according to case 4 described above. In addition, the magnitude of main area 355 is increased with the determination of curvature points 320, 325, and 330. Upon determining curvature point 335 lying below $+CRV_{thresh}$ 290, the magnitude of final area 360 is calculated for the region below curvature lobe 285 and between curvature point 330 and the intersection with $+CRV_{thresh}$ 290. Curvature points 335, 340 and 345 lie in the dead-zone and do not contribute to an area calculation. The area of curvature lobe 285 is calculated to include the sum of initial area 350, main area 355 and final area 360.

In some examples, a value M of a counter is maintained by a processor to monitor sample-by-sample development of a lobe. When the 'start lobe' calculations are performed, the value for M is reset to zero and incremented with each subsequent point that remains outside the dead-zone. Values for M are illustrated at the different curvature points in FIG. 7.

To find the area under the curvature lobe, the value of M is set to zero and the initial area of a curvature lobe is computed as initial area$=(C_i+CRV_{thresh}) \cdot (C_i - CRV_{thresh})/(C_i - C_{i-1})$ when the lobe is started. For each successive curvature value, the value of M is incremented and the additional area contribution is computed as additional area$=-(M-1) \cdot C_i + M \cdot C_{i-1}$. When the lobe ends, the value of M is not incremented and the final area contribution is computed as final area$=M \cdot C_{i-1} + (C_i + CRV_{thresh}) \cdot (C_i - CRV_{thresh})/(C_i - C_{i-1})$. The sum of the initial, final, and all additional areas may then be multiplied by $\Delta T/2$ to find the area under the curvature lobe.

To find the first moment of the area under the curvature lobe, a similar approach is used. When the initial area of the curvature lobe is computed, the initial moment of the area is also computed as initial moment$=-\{C_1 + 2\ CRV_{thresh}\} \cdot \gamma^2$ where $\gamma = (CRV_{thresh} - C_{i-1})/(C_i - C_{i-1})$. For each successive curvature value in the lobe, an additional moment contribution is computed using the same M values as for the area computations. This additional moment contribution is computed as additional moment$=\{C_i \cdot (3M-1) + C_{i-1} \cdot (3M-2)\}$. When the lobe ends, a final moment contribution is computed at the same time that the final area is computed. The final moment is computed as final moment$=[CRV_{thresh} \cdot \{3M+2\gamma\} + C_{i-1} \cdot \{3M+\gamma\}] \cdot \gamma$.

The sum of the initial, final, and all additional moments may then be multiplied by $\Delta T^2/6$ to find the first moment of the area under the curvature lobe. The time of the centroid of the curvature lobe area is found by dividing the first moment of the curvature lobe area by the curvature lobe area as time=first moment of area/area. This time is with respect to the time of the curvature point that started the lobe.

For both the area and the first moment of the area, the calculations are constructed so that the contribution of each curvature sample may be summed into a total area or total first moment of the area as the samples are collected. Thus, for all calculations, the factors include the present and previous curvature values, the threshold values, and the counter M. In this manner the area and the time of the centroid of the area are generated as soon as the lobe is ended.

Establishing Significant Points in a Sensed Cardiac Signal

SPs are established by point-by-point processing of a sensed cardiac signal. In some examples, the SPs in the signal are detected and saved into a buffer. In some examples, each SP has a set of values including the time of occurrence of the SP, the amplitude of signal at that time, and a value describing the degree (e.g., the direction and extent) of the turn or curve in the cardiac signal that produced the SP.

In some examples, SPs of an electrogram or electrocardiogram are extracted by sampling at 400 Hz. In some examples, sampling is performed at 200 Hz. The sampled data is filtered using a 5-point (400 Hz) or 3-point (200 Hz) running average filter and a five-point least squares regression average-point curvature method to select SPs relating to the QRS complex.

For detecting curvatures associated with slower morphologies, sampling is at a slower rate, such as, for example, 50 Hz. An example of a wave having slower morphologies would be the T-wave in a cardiac signal.

According to some examples, multiple sampling rates are used for SP extraction. In certain examples, dual-rate sampling is performed with sampling at 200 Hz providing fast SPs and sampling at 50 Hz providing slow SPs and a 3-point running average filter is used. In illustrative dual-rate sampling example, 200 Hz is used to provide fast SPs and 50 Hz is used to provide slow SPs, with 5-point least squares regression size and 3-point running average filtering at both rates.

In some examples, curvature is found by using 5-point least squares regression filtering. The coefficients for finding the linear (Bi) and parabolic (Ci) fit coefficients in the cubic least squares regression to the data ($D_{i-2}$ to $D_{i+2}$) at the point i are as follows:

| Linear | Parabolic |
| --- | --- |
| $P_{-2} = (1/12) * Rate$ | $Q_{-2} = (10/70) * Rate^2$ |
| $P_{-1} = (-8/12) * Rate$ | $Q_{-1} = (-5/70) * Rate^2$ |
| $P_0 = 0$ | $Q_0 = (-10/70) * Rate^2$ |
| $P_1 = (8/12) * Rate$ | $Q_1 = (-5/70) * Rate^2$ |
| $P_2 = (-1/12) * Rate$ | $Q_2 = (10/70) * Rate^2$ | where Rate is the sampling rate in sample/sec, Bi is the sum of the products of these P least squares regression coefficients multiplied by the 5 corresponding data points centered on i ($D_{i-2}$ to $D_{i+2}$) and Ci is the sum using the Q least squares regression coefficients. Curvature is then computed as:

$$Curvature = \frac{2 \cdot Ci \cdot W}{[1 + \{Bi \cdot W\}^2]^{3/2}}.$$

where W is a constant. Since W appears in conjunction with fit coefficients Ci or Bi, the value can be incorporated into the computations as a data signal gain such that $D'(i) = W \cdot D(i)$. Then, the curvature expression becomes $$Curvature = \frac{2 \cdot C'i}{[1 + \{B'i\}^2]^{3/2}}.$$

where B'i and C'i are found using the D' data points rather than the D data points with the least squares regression coefficients.

The expression for curvature may then be rewritten as:

$$Curv' = Curvature \cdot Gn = \frac{C'i \cdot 2 \cdot Gn}{[1 + \{B'i\}^2]^{3/2}} = \frac{C''i}{[1 + \{B'i\}^2]^{3/2}}.$$

where Gn is an arbitrary value which is incorporated (with 2) into C''. If the curvature thresholds used for detection of SPs is adjusted accordingly, it does not matter whether point-by-point curvature or Gn times the point-by-point curvature is calculated. Incorporating the values 2·Gn into C''i can be accomplished by changing the least squares regression coefficients $Q_{-2}$ through $Q_2$ into new least squares regression coefficients ($Q'_{-2}$ through $Q'_2$) by multiplication with 2Gn. If Gn is selected as 7/(6 Rate) and the term Fn=Rate/12 is incorporated as additional data signal gain, then the least squares regression coefficients become:

| Linear | Parabolic |
| --- | --- |
| $P''_{-2} = 1$ | $Q''_{-2} = 4$ |
| $P''_{-1} = -8$ | $Q''_{-1} = -2$ |
| $P''_0 = 0$ | $Q''_0 = -4$ |
| $P''_1 = 8$ | $Q''_1 = -2$ |
| $P''_2 = -1$ | $Q''_2 = 4$ | with $D''(i) = 2 \cdot W \cdot Fn \cdot D(i)$; and with $Ci'' = Q''_{-2} \cdot D''(i-2) + Q''_{-1} \cdot D''(i-1) + Q''_0 \cdot D''(i) + Q''_{+1} \cdot D''(i+1) + Q''_{+2} \cdot D''(i+2)$; and with $Bi'' = P''_{-2} \cdot D''(i-2) + P''_{-1} \cdot D''(i-1) + P''_0 \cdot D''(i) + P''_{-1} \cdot D''(i+1) + P''_{+2} \cdot D''(i+2)$.

Note that the coefficients are all powers of two (either 0, 1, 2, 4 or 8), thus simplifying hardware or firmware implementation of the present subject matter.

When using two sample rates for determining SPs, the computed curvatures will be different when computed at different rates. Thus, two threshold levels and parallel sets of computations are used. Also, the running average filtering is different with the fast rate filtering using five consecutive points while the slow rate filtering uses every fourth point spaced over sixteen points. In some examples, the fast and the slow running average filtering operations are performed in parallel.

In some examples, the linearity of the least squares regression operation is used. The running average filtering operation is performed at the fit coefficient level (i.e. the Bs and Cs) rather than the data level. In this embodiment, two filtering operations are performed (one for Bs, one for Cs) at each rate.

Using these methods of calculating curvature, SPs can be established in a sensed and sampled cardiac signal. Starting from the time of a first sample, a second sample is acquired so that the actual sample reflects the nature of the signal between the last sample and the current sample. At the actual time of the sample, the value of the sample may be ascribed to the time half-way between the current sample and the previous sample. Samples at the slow sample rate apply to the signal two fast sample steps earlier than the actual sample time.

In one embodiment, a circular data buffer is used. Data is acquired at the fast sample rate and used to fill a circular data buffer. Once the timing of a fast or slow significant point is determined, the data value for that significant point is found from the data stored in the circular buffer. Thus, the data buffer is sized so that the requisite data is still available in the buffer. In one embodiment, the buffer is sized to hold about 500 millisecond of data or 256 data points. In one embodiment, the circular buffer is implemented as a memory array with an index pointer. In one embodiment, the index pointer includes a binary counter and the buffer size is a power of two.

In one embodiment, running average filtering (RAF) is performed on the input data. In various embodiments, the filtering is provided by a circular buffer or a shift register set. The values in the circular data buffer reflect the fast running average filtering. In one embodiment, a hybrid approach is used where the fast running average filtering is performed and then the data is placed into a circular buffer.

In one embodiment, running average filtering reduces curvature noise relative to the signal content of fast curvature signals. An electrocardiogram signal typically takes relatively large excursions away from zero curvature at the times of fast turns in the signal. However, when the fast turns are less severe, the curvature signal does not move as far away from zero and curvature noise can prematurely end the curve lobe. The result is that one small curvature lobe is broken into two or more even smaller lobes. Thus, in one embodiment, the curvature noise relative to the signal content is reduced, for fast curvature signals, by running average filtering.

Filtering of the input signal does not achieve the same effect as filtering the actual curvature signals. In one embodiment, 3-point running average filtering is applied to the fast curvature values.

In one embodiment, fast curvature values are computed as average point curvature and 3-point running average filtering of the curvatures so that the fast curvature value computed when the current sample is taken applies to a time in the input signal that is five time steps earlier than the current sample.

In one embodiment, slow curvature values are computed at ¼ the fast sample rate and are computed as average-point curvatures so that when the every fourth fast sample is taken, slow curvature is computed and it applies at a time in the input signal that is four slow (sixteen fast) time steps earlier than the current sample.

In one embodiment, the detection of a curvature lobe and significant points generation entails both fast and slow characteristic point generation performed in parallel. In one embodiment, separate curvature thresholds and curvature area thresholds are used for the fast and slow operations.

In one embodiment, a curvature lobe is ended when the curvature signal crosses the same threshold used to start the lobe but in the opposite direction of the crossing that started the lobe. In one embodiment, a hysteresis is used so that a curvature lobe is ended when the curvature signal crosses a threshold that is smaller (i.e. closer to zero) than the threshold used to start the lobe but in the opposite direction of the crowing that started the lobe. In one embodiment, a curvature lobe is ended when the curvature signal crosses zero as the hysteresis value.

In one embodiment, the value of W is selected according to the following procedure. Select an approximate range for W from the following analysis. At a 200 Hz sampling rate, the QRS takes approximately five samples. The signal at the peak is approximated by 128. If the QRS were to be approximated (in curvature space) as a semicircle arching from zero to the peak then back to zero in five points, then the radius of that semicircle would be 0.01 sec and the peak would have a value of 0.01. Thus, the value of W would be the one that, when multiplied, the peak (128) would have the value of 0.01, i.e. $W=0.01/128=0.000078$. In one embodiment, $W=0.000122=1/8192$ which is a power of two.

In some examples, curvature thresholds reduce or eliminate the noise significant points and computational burden. This noise is the natural results of the curvature signal hovering around zero (or some other value) when the raw signal does not otherwise have significant turnings.

In some examples, for a curvature lobe to be detected, the point-wise curvature falls outside of a dead-band formed by the threshold values on either side of zero. Reducing this threshold towards zero increases the number of curvature lobes that are detected and increases the computational burden. In some examples, a threshold value is selected by using approximately a 1 minute epoch of the input signal to make a histogram of the fast curvature values computed at each sample time. The threshold value is selected as one which corresponds to 20% of the peak. This value is then used as the threshold for both the fast curvature and slow curvature feature selection process.

In some examples, the noise lobes are removed by requiring that a detected lobe must exceed a critical area limit. The noise lobes have generally small areas while the real lobes associated with characteristic turns in the signal usually have substantial areas.

In some examples, different values are used for the fast curvature and slow curvature area thresholds. Using the number of beats occurring in the one minute epoch used to set the gain and curvature thresholds, select a desired number of fast and slow characteristic points to find for these beats. For instance, five fast significant points per beat and eight slow significant points per beat may be used as targets. The area thresholds are then adjusted until these target numbers of significant points are found. In one embodiment, a lower area limit of 0.1 is used.

In some examples, a template is established for classifying beats. For example, a significant point template includes a rectangular box covering a time (relative to a fiducial significant point) and signal amplitude. The template also includes a curvature area sign. A discussion of establishing characteristic points, or significant points, for a sampled cardiac rhythm signal can be found in Sweeney et al., "Tachyarrhythmia Detection and Discrimination Based on Curvature Parameters," U.S. Patent Pub. No. US 2007.0203419, filed Jun. 27, 2003, which is incorporated herein by reference in its entirety.

Estimating Heart Rate Using Significant Points

Once the SPs have been established in the sensed cardiac signal, heart rate of the signal can be estimated. Heart rate in beats per minute (bpm) is estimated by forming the following:

$$\text{Beats/minute} = (\text{No. of SPs per second} * 60) / \text{No. of SPs per heart beat}.$$

The number of SPs per second is found by dividing the number of SPs in a cardiac segment by the time between the first SP of the segment and the last SP of the segment.

Figure 8:
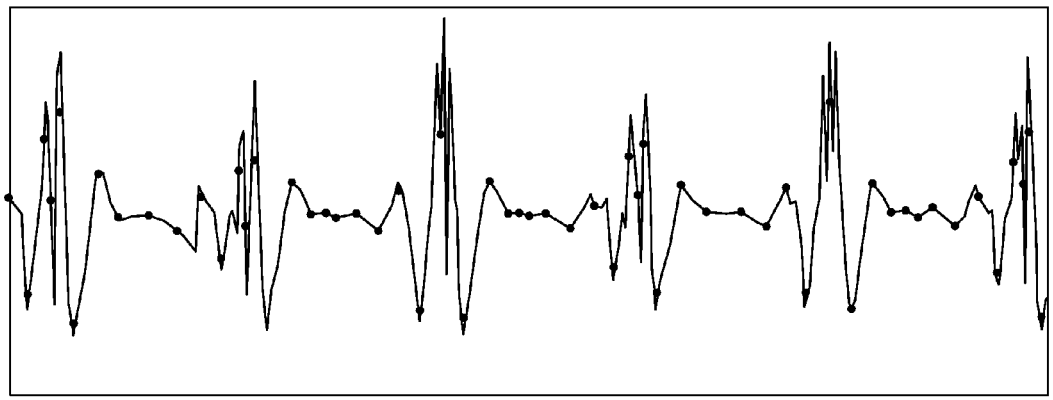
FIG. 8 shows an example of an electrogram during an episode of monomorphic ventricular tachycardia.

FIG. 8 shows an example of an electrogram during an episode of monomorphic ventricular tachycardia (MVT). The Figure shows a few seconds of the rhythm along with the SPs indicated by the dots. In this example, the SPs are only represented by times and values of the sensed cardiac signal. In the signal segment shown, the individual beats have about 10 to 12 SPs each. The entire VT episode had 38.1 SPs/sec.

The number of SPs/beat is found using an autocorrelation in the SP-domain. In the autocorrelation, SPs are shifted and multiplied to form a product. Because the autocorrelation is in the SP-domain, the SPs are shifted by a number of SPs instead of shifted by an amount of time. Similar to autocorrelation in the time domain, the SP autocorrelation value starts at 1 when each SP is multiplied by itself to form the first product. The subsequent products are formed by shifting one SP, then two SPs, then three SPs, etc. As the values are shifted and the products formed, the autocorrelation value changes. When the SP shift best approaches the number of SPs per beat, the SP-domain autocorrelation has a peak.

As explained previously, an SP corresponds to a time of occurrence of a turn in the cardiac signal, a degree or extent of the turn, the amplitude of the cardiac signal for the turn, and the area of the turn (which describes the degree and direction of the turn). The SPs are multiplied by multiplying like metrics of the SPs. In forming the products, it was determined that forming the products from the value of the signal at the turn by the area of the turn (metric=$SP_{value} * SP_{area}$) was effective in determining SPs/beat. Other autocorrelations are possible, such as by auto-correlating other like metrics of the SPs or forming the autocorrelation of the SPs in the time domain.

The $SP_{area}$ is a signed value that describes the degree and direction of the turn in the signal. Large areas area associated with pronounced turns of longer durations. The $SP_{value}$ is the amplitude of the sensed cardiac signal at the times of the SP. The $SP_{value} * SP_{area}$ metric describes both the direction and duration of the turn in the cardiac signal as well as the amplitude. For N SPs, the value of the SP autocorrelation for a shift of K is $$SPAutocorrelation = \frac{\sum_{I=1}^{I=N-K} SP_{value}(I+K)*SP_{area}(I+K)*SP_{value}(I)*SP_{area}(I)}{\sum_{I=1}^{I=N} SP_{value}(I)*SP_{area}(I))^2}.$$

Figure 9:
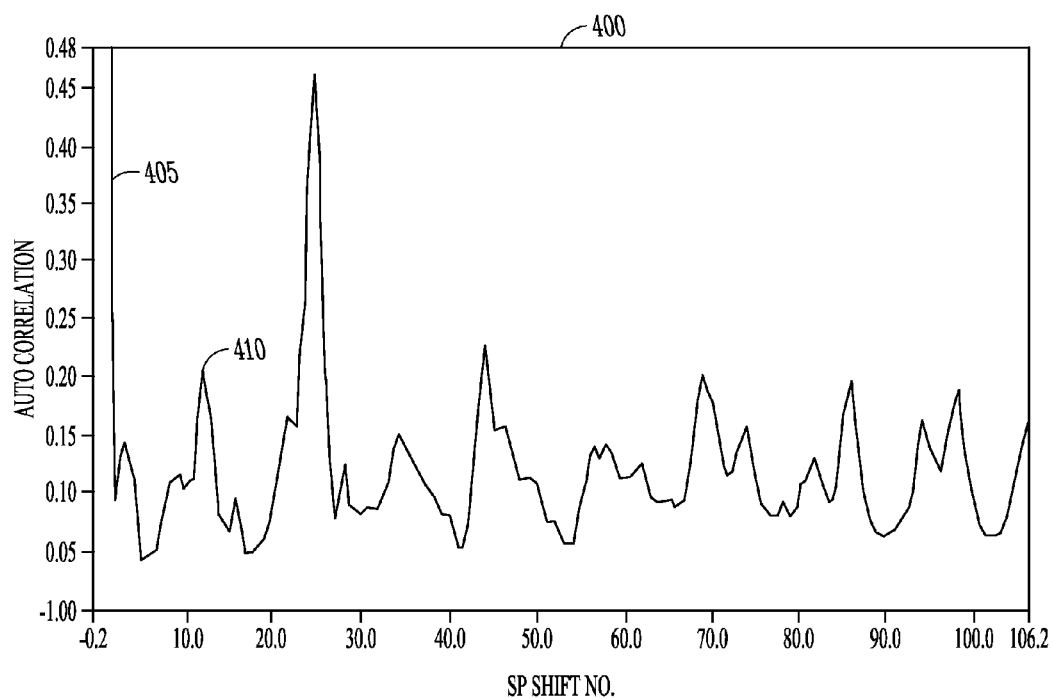
FIG. 9 shows a graph of an example of an SP autocorrelation for the episode of FIG. 8.

FIG. 9 shows a graph 400 of an example of an SP autocorrelation 405 for the VT episode of FIG. 8. The Y-axis is the auto correlation value and the X-axis is the SP shift. It can be seen from the Figure that the SP autocorrelation includes sub-harmonics indicated by the multiple peaks in the autocorrelation. These sub-harmonics frequencies are multiples of the fundamental frequency of the heart rate of the rhythm. In this case, the heart beat pattern of the MVT is repeated at regular intervals. The autocorrelation exhibits a first peak 410 at a shift index of 12. This leads to an SP-based rate estimate of (38.1 SP/sec)/(12(SP/beat)=3.175 beats/sec=190 bpm.

In the ideal case, the underlying rate is described by the first peak in the autocorrelation. However, selecting the first peak in the autocorrelation is not always straightforward. The underlying rhythms are not comprised of perfectly repeated beats; making the sub-harmonics not always easy to identify. As shown in FIG. 9, the autocorrelation includes numerous small peaks and there are later peaks that are larger than the earlier peaks. This is because the underlying rhythms are not comprised of perfectly repeated beats in non-ideal cases and there may be noise or other signal artifacts present. The challenge is to locate the "correct" peak to use in the heart rate estimation.

Figure 10:
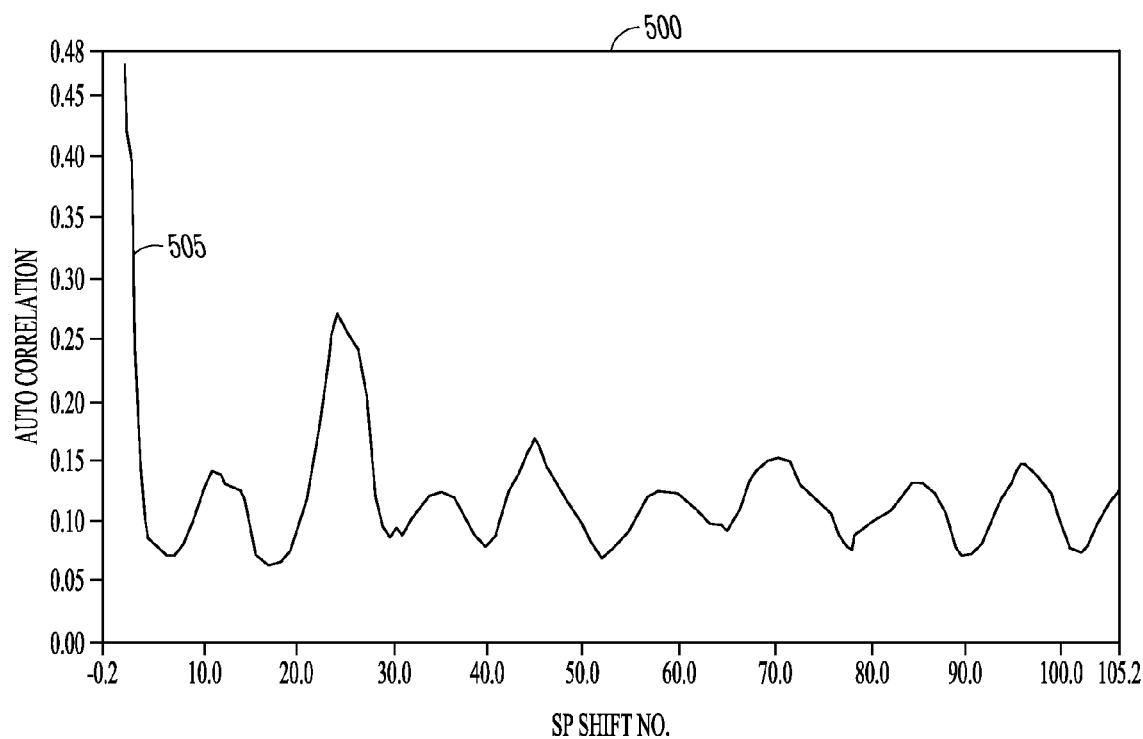
FIG. 10 shows a graph an example of the SP autocorrelation of FIG. 9 after filtering.

One approach to enhance determination of the correct peak is to filter the autocorrelation to remove the influence of the lesser peaks. FIG. 10 shows a graph 500 an example of the SP autocorrelation of FIG. 9 after 5-point running average filtering of the autocorrelation. Note that the smaller peaks are removed and the height of the peaks is more uniform in the filtered SP autocorrelation 505.

Another approach is form an autocorrelation of the SP autocorrelation. For simplicity the first autocorrelation (e.g., the autocorrelation of FIG. 9) is referred to as SP1 autocorrelation. The SP1 autocorrelation has an amplitude for each SP-shift. The autocorrelation of the SP1 autocorrelation is referred to as SP2 autocorrelation. The SP2 autocorrelation is also in the SP domain, but is based on the amplitudes of the SP1 autocorrelation at each SP-shift. In the SP1 autocorrelation, peaks at sub-harmonics of the underlying period appear as multiple peaks in the autocorrelation. The first peak of SP1 corresponds to repetitions of the underlying beat in the signal. The second peak of SP1 corresponds to repetitions of sets of two beats, and so on. In this way, the periodicity of the SP1 autocorrelation itself reveals additional information about number of SPs/beat.

In some examples, in preparation for the SP2 autocorrelation, trends are removed from the SP1 autocorrelation by fitting a least-squares regression to the unfiltered values of the SP1 autocorrelation starting at the third shift point of the SPs and higher. This fit is then subtracted from all values in the SP1 autocorrelation which is then filtered (e.g., by 3-point running average filtering).

Figure 11:
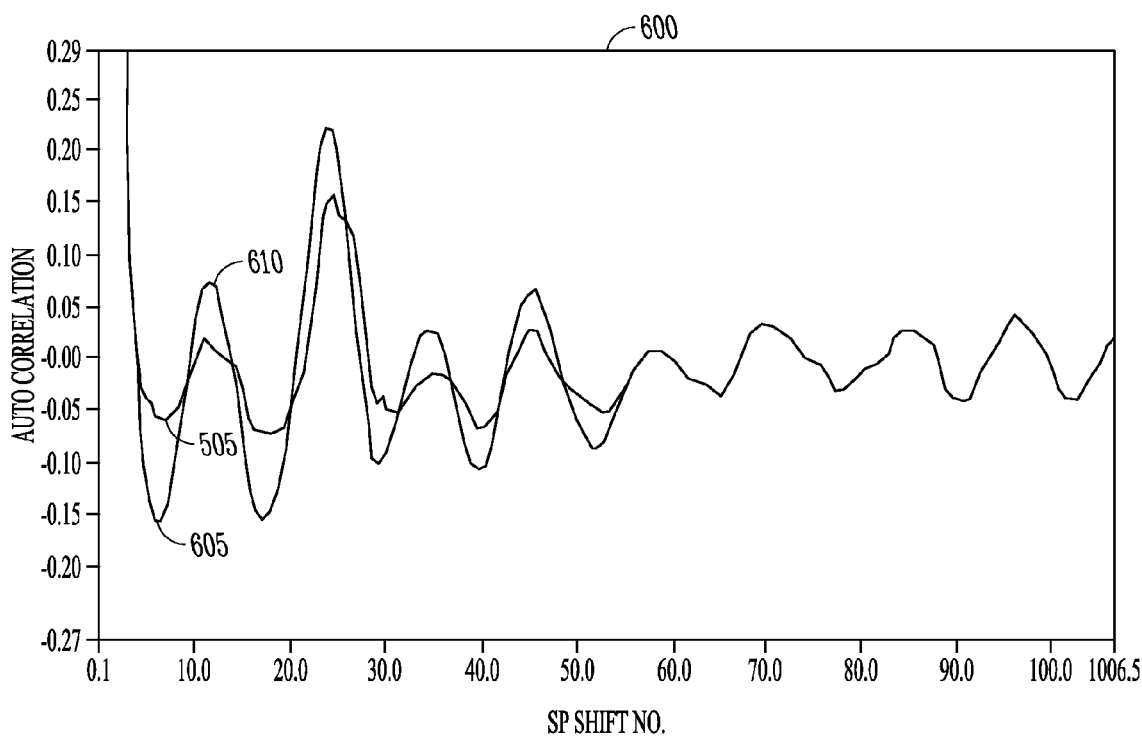
FIG. 11 shows a graph of an autocorrelation of the SP autocorrelation of the rhythm of FIG. 8.

FIG. 11 shows a graph 600 of the SP2 autocorrelation 605 that is a de-trended SP1 autocorrelation of the rhythm of FIG. 8. Also shown is the filtered SP1 autocorrelation. The first peak 610 of the SP2 autocorrelation is a better representation of the basic period in the cardiac signal. The first peak 610 occurs at an SP shift of 11.375 and leads to an SP-based rate estimate of (38.1 SP/sec)/(11.375(SP/beat)=3.349 beats/sec=201 bpm.

A device-based rate estimate of the rhythm of FIG. 1 was determined to be 205 bpm using the rate sensing channel of an IMD. Thus, the SP2 autocorrelation better matches the device-based estimate than the SP1 autocorrelation alone.

Figure 12:
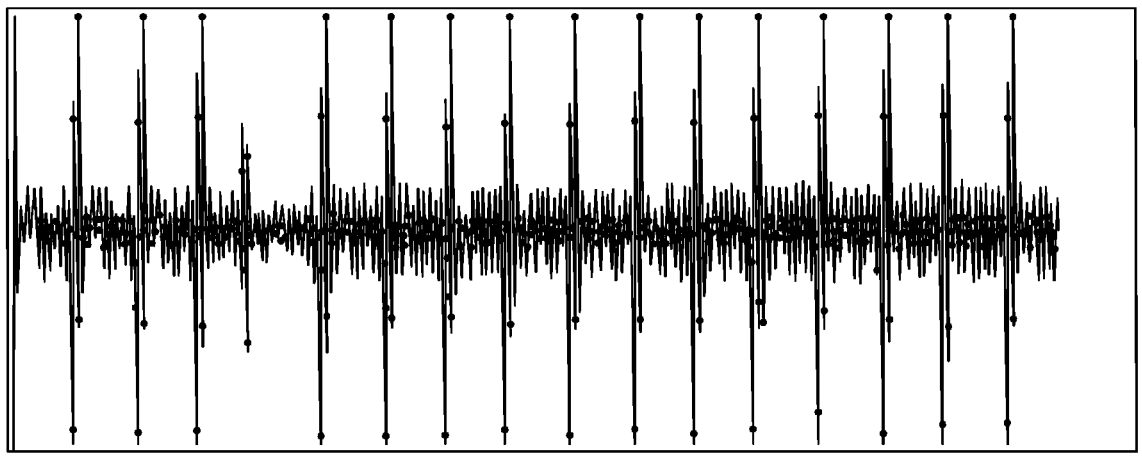
FIG. 12 shows a graph of an example of an electrogram of a normal heart rhythm with noise.

FIG. 12 shows a graph of an example of an electrogram of a sensed cardiac signal representing normal heart rhythm with noise. Inspection shows there is an underlying rhythm of about 72 bpm. However, because of the noise, a device may determine the rate to be much higher (about 240 bpm) using rate channel sensing and deliver an inappropriate shock.

Figure 13:
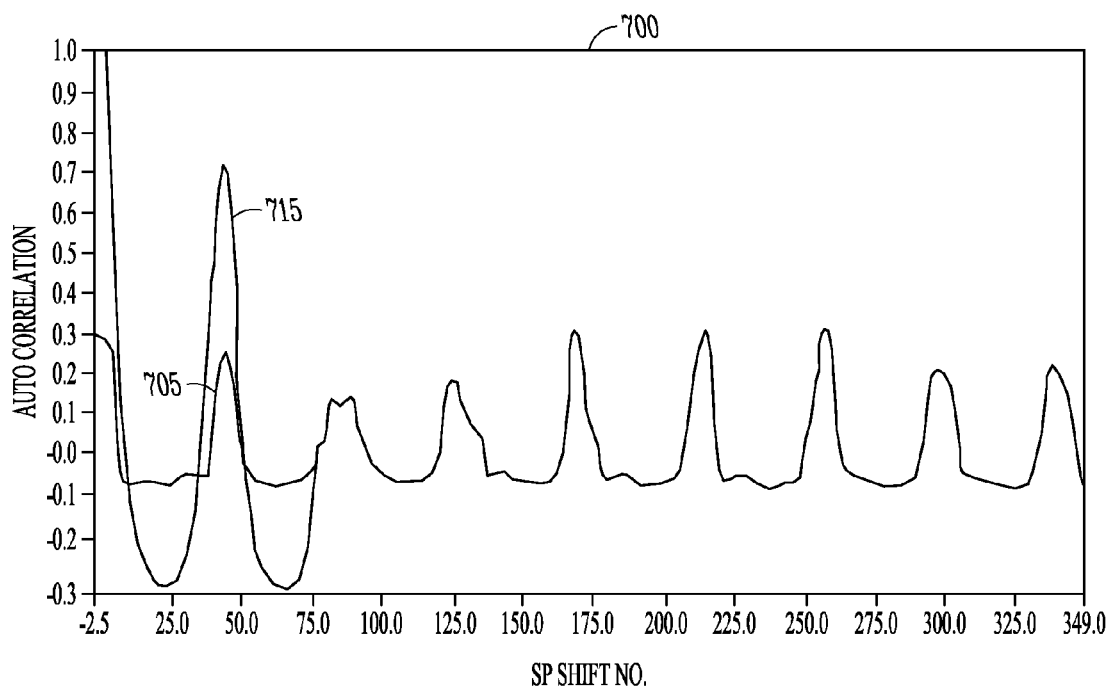
FIG. 13 shows a graph of an autocorrelation of the SP autocorrelation of the rhythm of FIG. 12.

FIG. 13 shows a graph 700 of the SP2 autocorrelation 715 and the SP1 autocorrelation 705 of the rhythm of FIG. 12. There is a clear pronounced peak at an SP shift of 43.125. Because the rhythm had 51.5 SP/sec, the SP-based rate is determined to be 71.6 bpm, which is very close to the actual rhythm rate. Device-based rate channel sensing determined the rate to be 240 bpm. Thus, the device-based rate is high and could lead to an inappropriate shock.

Figure 14:
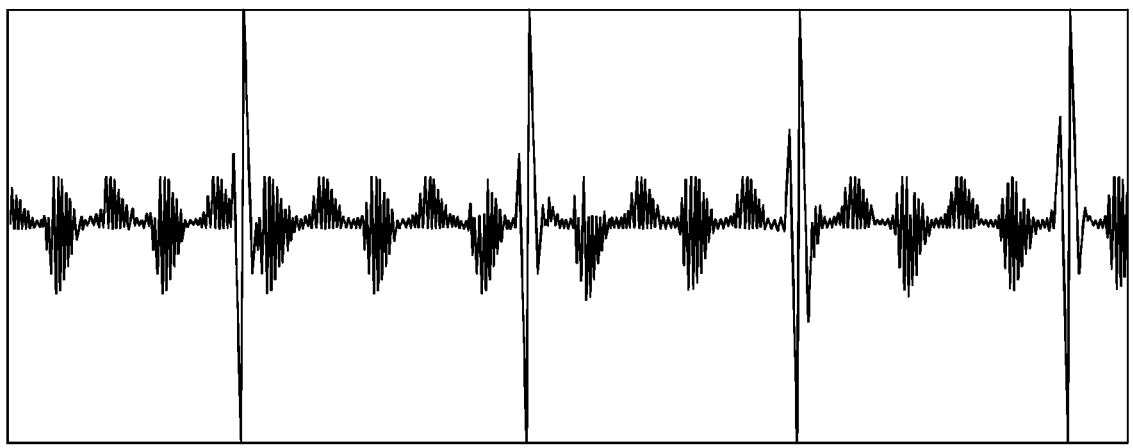
FIG. 14 shows a graph of another example of an electrogram of an episode of tachyarrhythmia where the electrogram includes noise.

FIG. 14 shows a graph of another example of an electrogram of an episode of tachyarrhythmia where the electrogram includes noise. This episode is more problematic in determining rate than the episode of FIG. 12. The underlying rhythm is about 45 bpm but has a noise artifact that appears to be about 50 Hertz. The period of the noise appears to be interacting with the sampling rate to form an envelope beat frequency of about 122 bpm. The electrogram has about 91 to 94 SPs per heart beat. Because of the noise, a device may determine a higher rate than the actual rate (about 198 bpm) using the rate channel and deliver a shock.

Figure 15:
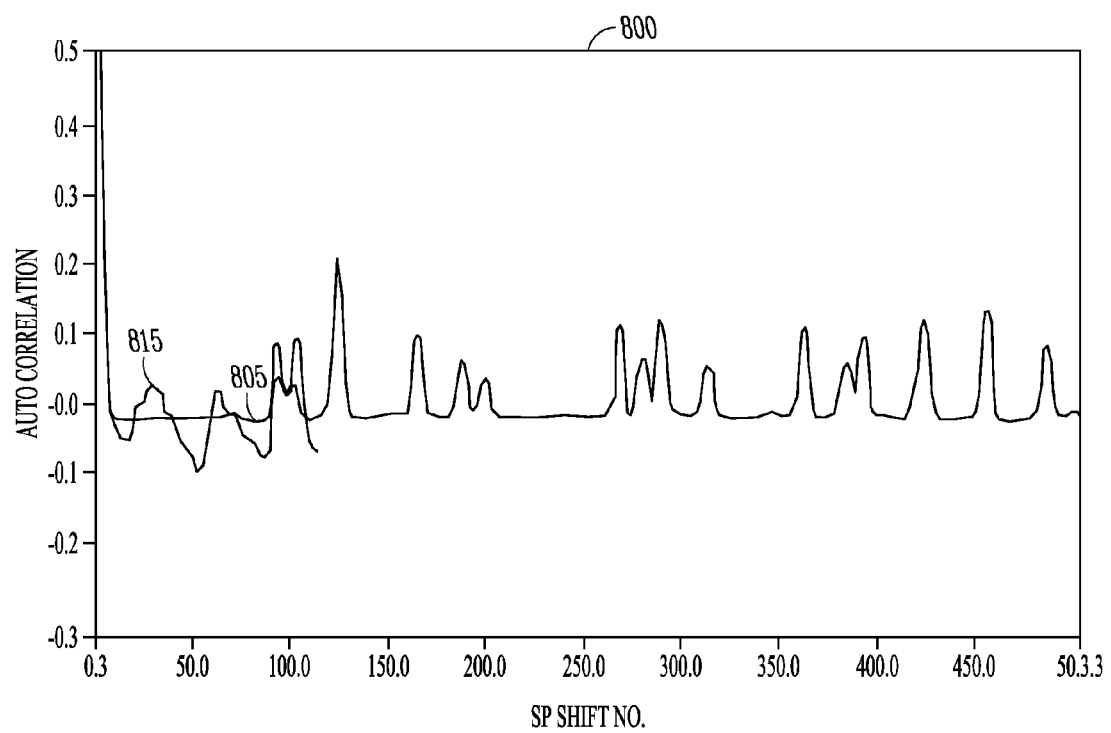
FIG. 15 shows a graph of an autocorrelation of the SP autocorrelation of the rhythm of FIG. 14.

FIG. 15 shows a graph 800 of the SP2 correlation 815 and the SP1 autocorrelation 805 of the rhythm of FIG. 14. Unlike the graphs of FIGS. 9, 11 and 13, the SP2 autocorrelation of FIG. 15 has multiple possible choices as the first peak. There are multiple peaks at SP shifts of about 30, 62, 94, and 103.5. Because the electrogram has 75.7 beats/sec, the peaks represent heart estimates of 151 bpm, 73 bpm, 48 bpm, and 44 bpm respectively. Choosing the correct peak for the rate estimate is important to accurately determine the underlying heart rate. Choosing an incorrect peak may lead to inappropriate therapy.

Sometimes the correct peak can be identified through a relatively simple selection or "filtering" or process. It was observed from data that most rhythms with noise have SPs with an $SP_{area}$ of −0.1 and 0, and a difference in $SP_{value}$ between the SPs of less than about 0.2. Thus, in some examples, the simple filtering includes determining if the first SP of the candidate peak of the SP2 correlation has a negative value of $SP_{area}$ and an $SP_{value}$ greater than the previous SP. In certain examples, the simple filtering includes determining if the first SP of the candidate peak has an $SP_{area}$ less than −0.1 and an $SP_{value}$ greater than the $SP_{value}$ of the previous SP by 0.2.

Figure 16A:
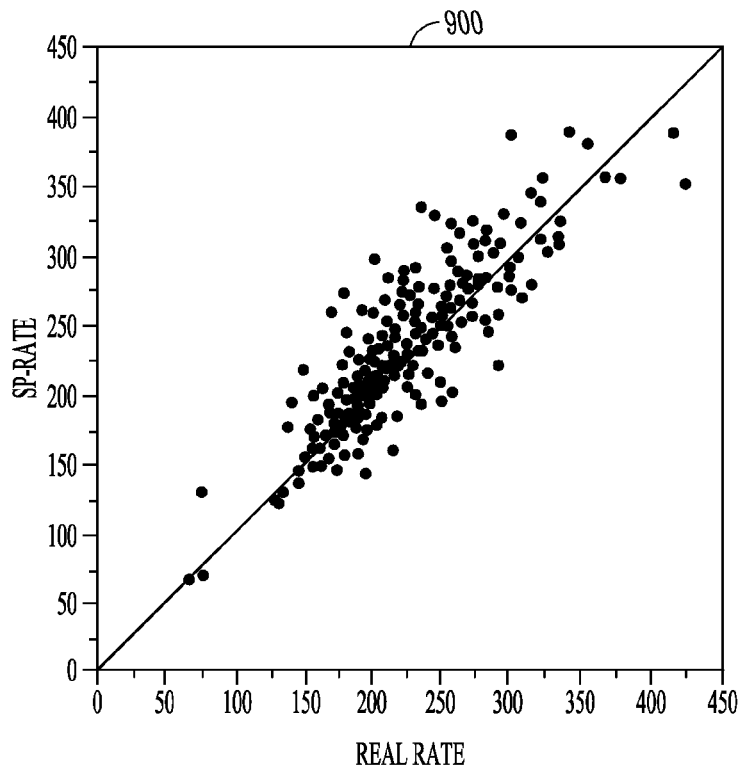
FIG. 16A shows a plot of the SP-based rate estimate versus the actual rate for a population of cardiac signals having autocorrelations that passed a simple filtering process.
Figure 16B:
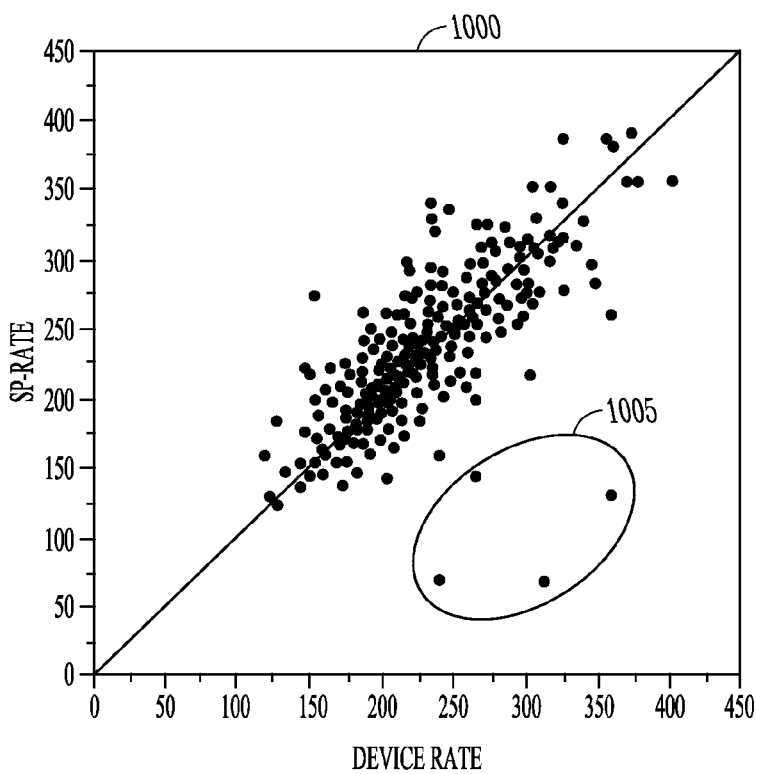
FIG. 16B shows a plot of the SP-based rate estimation versus a typical rate channel estimation.

FIG. 16A shows a plot 900 of the SP-based rate estimation versus the real or actual rate for a population of cardiac signals that have an SP2 autocorrelation that passed the simple filtering process. It can be seen from the Figure that the SP-based rate matches well with the actual rate. FIG. 16B shows a plot 1000 of the SP-based rate estimation versus a typical rate channel estimation. The SP-based rate estimation matches well with the rate channel-based estimation except for the four instances indicated by the circle 1005. For these four arrhythmias, the SP-based rate was significantly lower than the rate channel-based estimate. It was determined that these four arrhythmias contained noise but had a strong underlying rhythm in the electrograms with the result being that the SP-based rate was close to the actual rate, but was one-half or less than the rate estimated using rate channel sensing. Thus, the SP-based estimation more accurately determined the actual rate and would have prevented an inappropriate therapy resulting from falsely detecting a high rate.

If a detected arrhythmia does not pass the simple filtering described above, the correct peak for the rate estimate may be chosen by examining the string of SPs for the SP2 autocorrelation for the arrhythmia. SPs are identified that are associated with positive going peaks; starting with the first positive-going peak that has greater autocorrelation amplitude than the immediately preceding positive-going or negative-going peak. From these identified SPs, the SP with the maximum $SP_{value}$ is selected and the SP shift of the selected peak is used to determine the SP-based rate.

Figure 17:
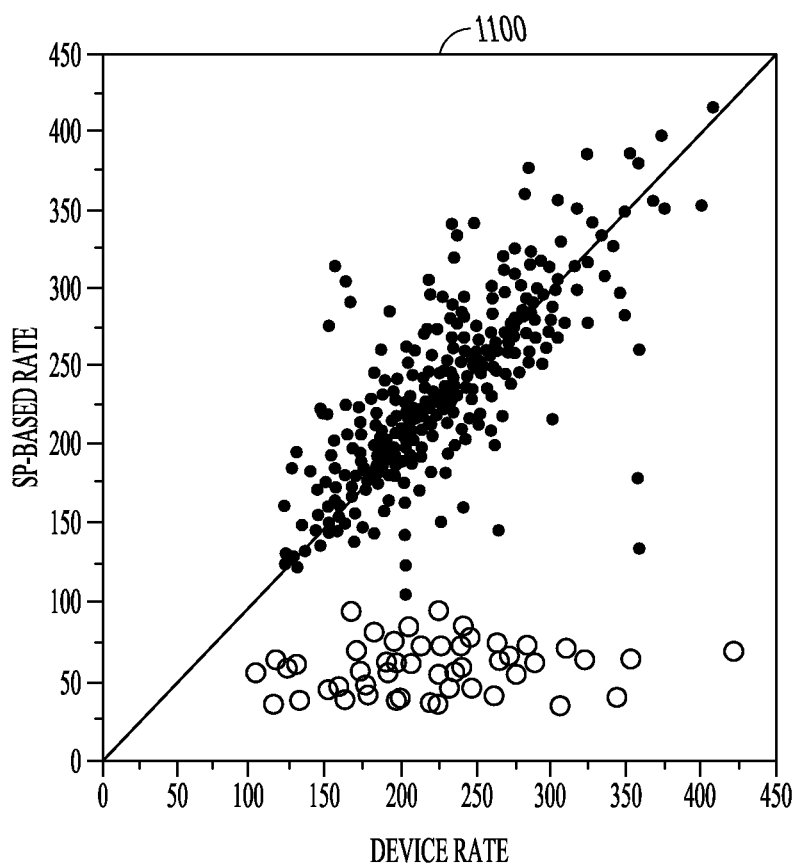
FIG. 17 shows a plot of the SP-based rate estimates versus rate channel determined rates for a population of sensed cardiac signals.

FIG. 17 shows a plot 1100 of the rate estimated using the SP-based methodology described above versus rate determined by a device using a rate channel for a population of sensed cardiac signals. Arrhythmias with SP-based rates lower than 100 bpm are indicated by the larger circles near the bottom of the plot 1100. Most of these arrhythmias were adjudicated as having noise present.

Figure 18:
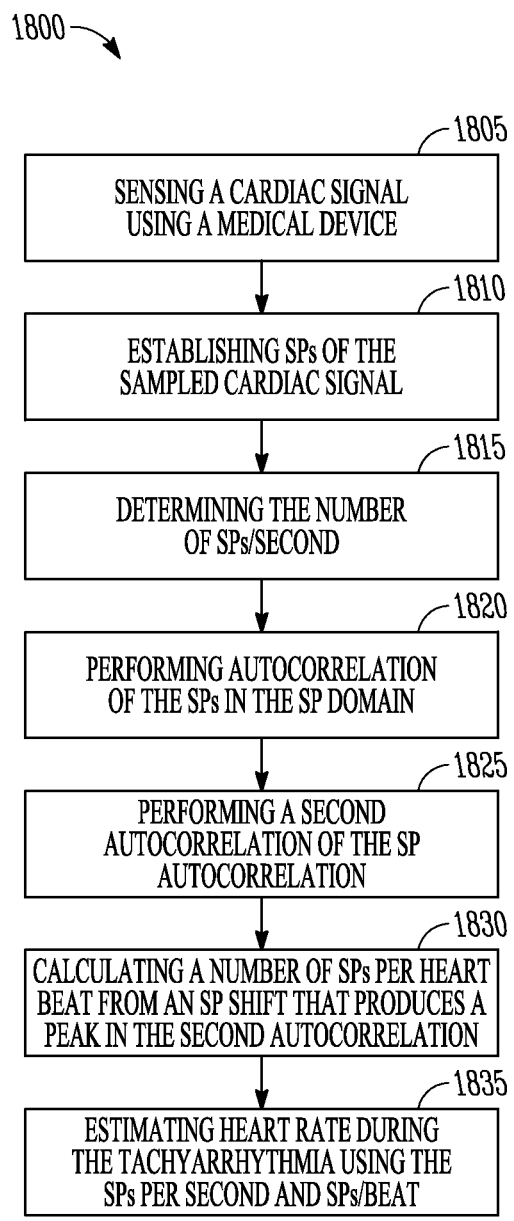
FIG. 18 shows an example of a method for determining heart rate using SPs.

FIG. 18 shows an example of a method 1800 for determining heart rate for a detected rhythm using SPs. At block 1805, a cardiac signal is sensed and sampled using a medical device such as a cardiac function management device (e.g., an implantable or wearable cardioverter defibrillator).

At block 1810, SPs are established for the sampled cardiac signal or electrogram. As explained previously, an SP corresponds to a time of occurrence of a turn encountered in the cardiac signal. In some examples, an SP includes at least a value of $SP_{area}$ that is a signed value that describes the degree and direction of the turn in the signal, and includes an $SP_{value}$ that is the amplitude of the sensed cardiac signal at the times of the SP. At block 1815, the number of SPs per second in the sampled cardiac signal is determined.

At block 1820, autocorrelation of the SPs is performed in an SP domain (SP1 autocorrelation). In some examples, the SP1 autocorrelation includes the autocorrelation of $SP_{area}*SP_{value}$ in the SP domain.

At block 1825, a second (SP2) autocorrelation of the SP1 autocorrelation is performed. In some examples, a trend of the SP1 autocorrelation is removed and the result smoothed in preparation for the SP2 autocorrelation. In some examples, this is done using running average filtering.

At block 1830, a number of SPs per heart beat is calculated from the SP shift that produces a peak in the second autocorrelation. In certain examples, the first peak of the SP2 autocorrelation is used. At block 1835, heart rate for the detected rhythm is estimated using the SPs per unit of time (e.g., per second) and SPs per beat.

Noise Estimation Using SPs

As explained above, the SP-based method is sometimes better able to accurately estimate rate in the presence of noise than a device-based rate channel method. It may be desirable to have a medical device withhold therapy during those arrhythmias that are adjudicated by the device as noise. Therefore, a medical device should make an estimate of the presence of noise in the detected arrhythmia. According to some examples, the noise in the signal can be estimated using the SPs. In some examples, the noise is estimated as the SPs are established or generated. In some examples, noise is estimated using SPs at the same time as SPs are generated to estimate heart rate. In some examples, the noise is estimated after rate is estimated using the SPs.

It can be seen from a comparison of FIG. 8 to FIG. 12 that the number of SPs and the number of SPs per unit time increase in the presence of signal noise. As indicated above, the electrogram of FIG. 8 has about 38 SPs/sec while the electrogram of FIG. 12, the noisier case, has about 51.5 SPs/sec.

Figure 19A:
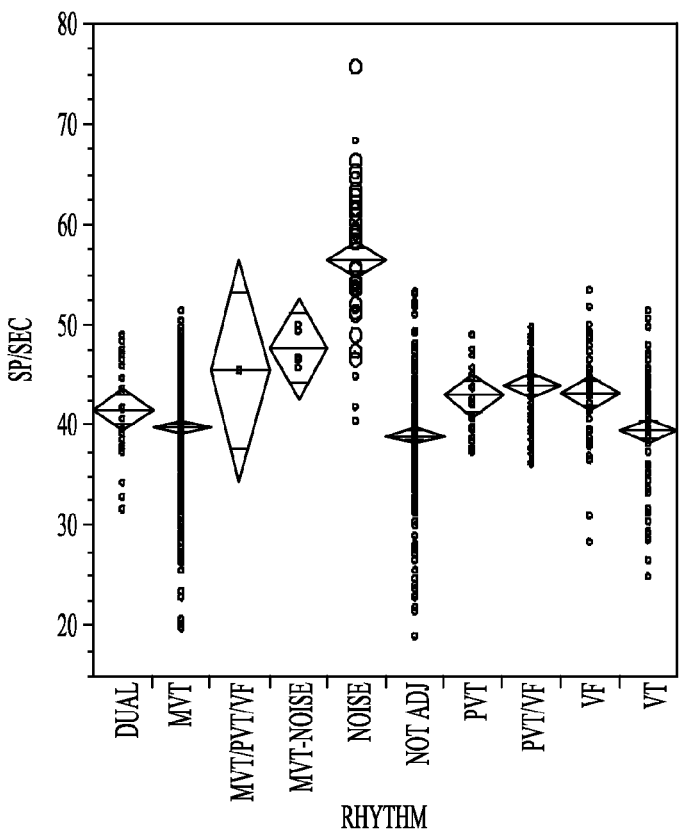
FIG. 19A shows a distribution of SP/sec for a population of cardiac signals.

FIG. 19A shows a distribution of SP/sec for a population of cardiac signals that were adjudicated to be noise and for signals adjudicated to be another type of tachyarrhythmia. Also shown is the SP/sec for those signals that were not adjudicated into noise or a particular rhythm. Note that the number of SPs/sec was typically higher for noise signals than for the other adjudicated signals.

Returning to FIGS. 8 and 12, further note that many of the SPs in FIG. 8 are close to the baseline value while in FIG. 12 most of the SPs are further away from the baseline. This suggests that the number of SPs per second that are more than a specified amplitude away from its previous SP may hold information about noise.

Figure 19B:
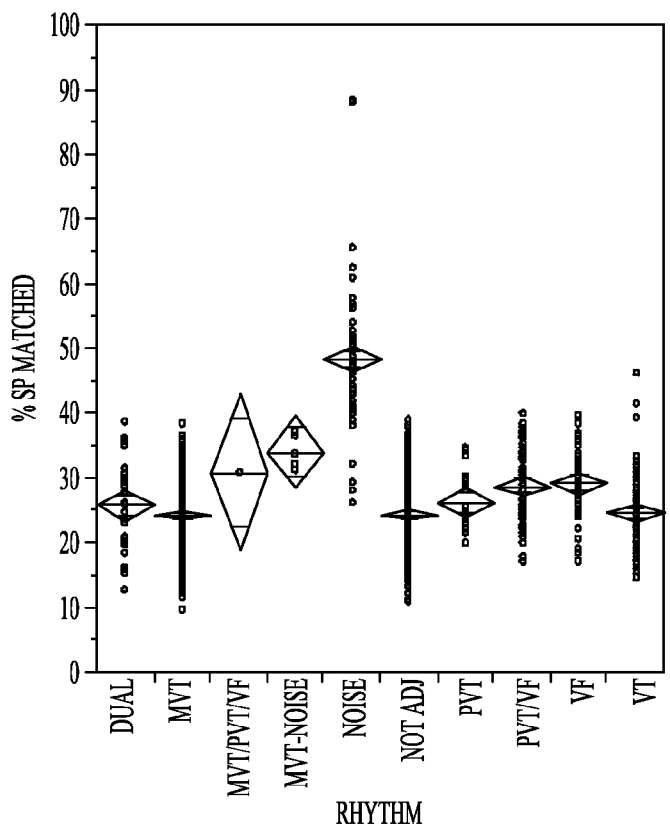
FIG. 19B shows a distribution of the percentage of SPs that were matched to the previous SP for the population of cardiac signals in FIG. 19A.
Figure 20:
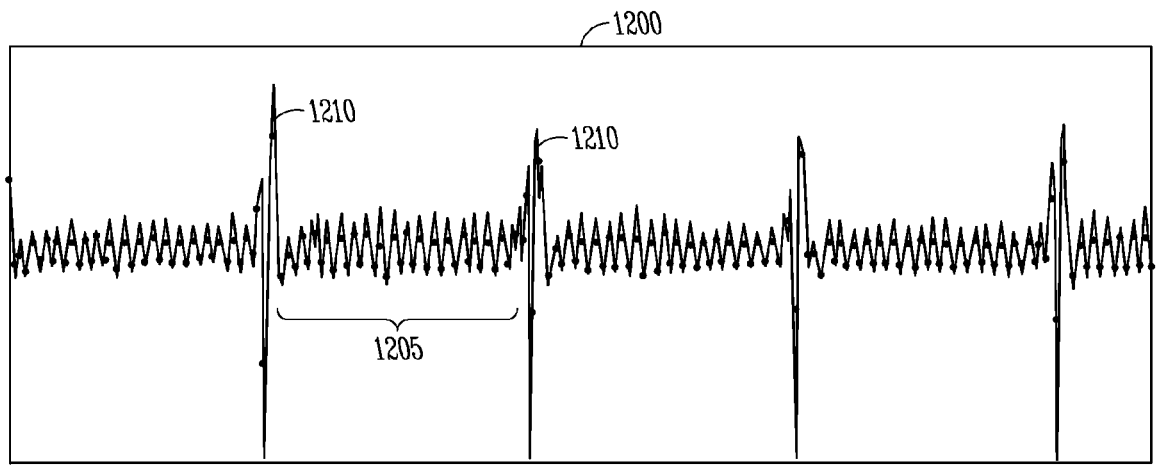
FIG. 20 shows a graph of another example of an electrogram of a heart rhythm with noise.

FIG. 20 shows a graph 1200 of another example of an electrogram of a heart rhythm with noise. Note that for the signal noise 1205 between the indications of depolarization 1210, the SPs usually come in pairs with a positive going noise spike matched to a similar negative going noise spike. This suggests that SP pairs that satisfy a specified matching criterion may provide information about noise. In some examples, the matching criterion includes those SPs that differ from the previous SP by an $SP_{value}$ equal and opposite to a previous signal amplitude difference. FIG. 19B shows a distribution of the percentage of SPs that were matched to another SP using the population of cardiac signals in FIG. 19A. Note that the percentage of SPs that were matched is typically higher for noise signals.

Figure 21:
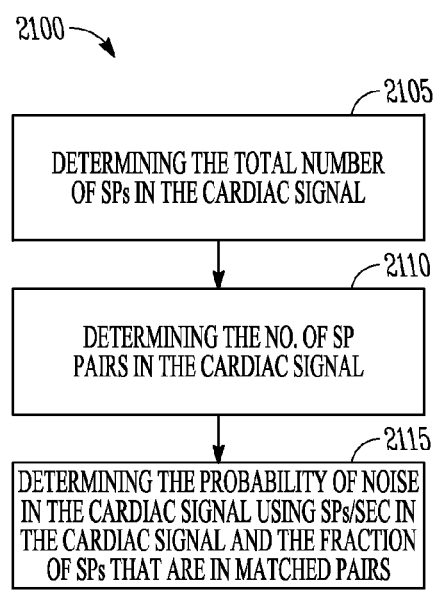
FIG. 21 shows an example of a method of estimating the presence of noise in a sensed cardiac signal.

FIG. 21 shows an example of a method 2100 of estimating the presence of noise in a sensed cardiac signal. At block 2105, the total number of established SPs (NumSP) is determined in a sampled segment of the cardiac signal.

At block 2110, the number of SP pairs is determined in the segment. In some examples, the number of SPs from the second SP to NumSP where the difference from the previous SP is roughly equal and opposite to the previous such difference, e.g.

$$\{SP_{value}[i]-SP_{value}[i-1]\} \cong -\{SP_{value}[i-1]-SP_{value}[i-2]\},$$

where roughly equal to ($\cong$) is, for example, between 50% and 150%. $SP_{matched}$ is the number of SPs that are included in matched pairs.

At block 2115, the probability of noise in the cardiac signal is determined using SPs/sec in the cardiac signal and the fraction of SPs that meet the matching criterion. In some examples, the probability of a sampled signal being a noise signal is determined as a logistic regression. In certain examples, the logistic regression is determined as $$Pr[\text{Noise}] = \frac{1}{\{1 + e^{([28.3-0.303*SP/\text{sec}]-[31.9*SPmatched/NumSP])}\}}.$$

Figure 22:
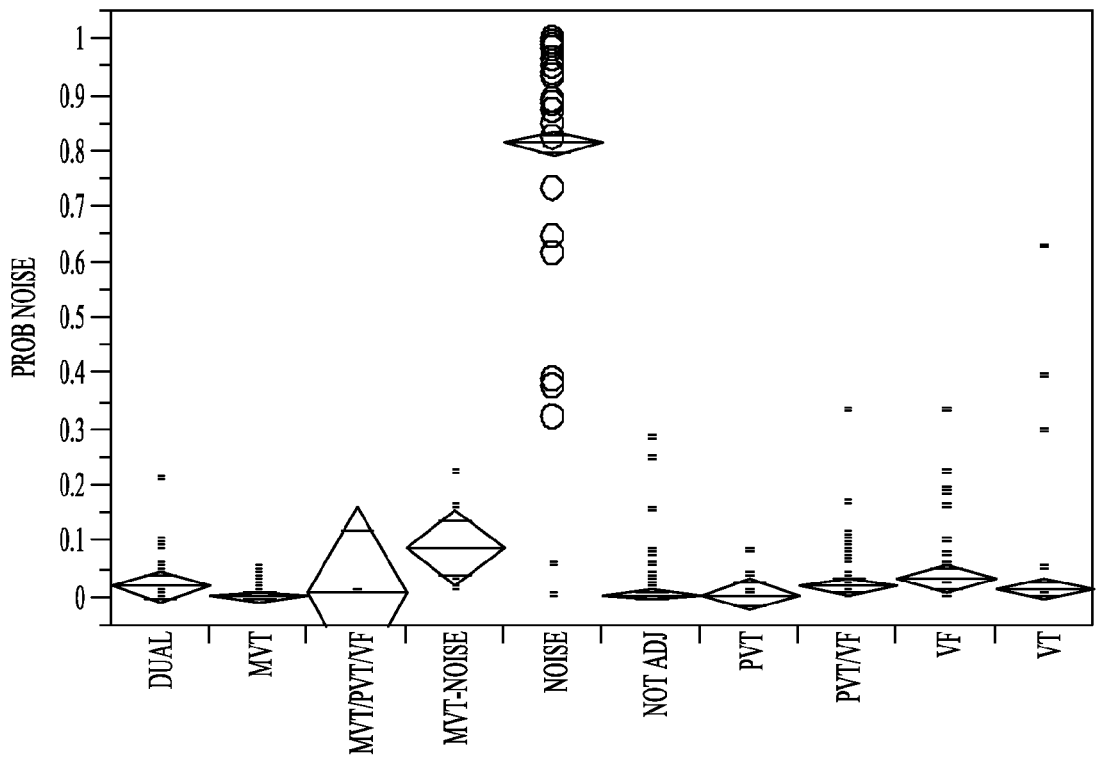
FIG. 22 shows the distribution of the calculated noise probability for the cardiac signals of the signal population in FIG. 19A and FIG. 19B.

FIG. 22 shows a distribution of the calculated noise probability for the cardiac signals of the signal population in FIG.

19A and FIG. 19B. The probability was calculated using the equation above. The distribution shows that there is not a lot of overlap in the calculated probability and the methodology works well to estimate the presence of noise in a sensed cardiac signal.

Implementation Examples

Significant points analysis can improve the ability of a medical device to correctly recognize and classify types of tachyarrhythmia and reduce the incidence of inappropriate shocks by the medical device.

Figure 23:
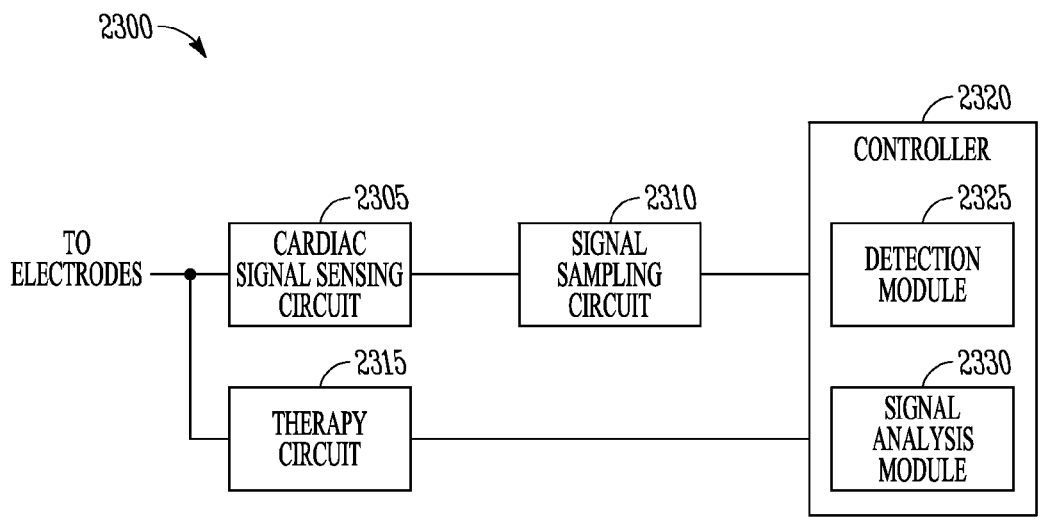
FIG. 23 shows an example of a block diagram of portions of a device to provide tachyarrhythmia therapy to a patient or subject.

FIG. 23 shows an example of a block diagram of portions of a device 2300 to provide tachyarrhythmia therapy to a patient or subject. The device 2300 includes a cardiac signal sensing circuit 2305 configured to provide a sensed electrical cardiac signal representative of cardiac activity of the subject and a sampling circuit 2310 coupled to the cardiac signal sensing circuit 2305 to generate digitized sampled values of the sensed cardiac signal. In some examples, the cardiac signal sensing circuit 2305 includes an implantable electrode and the sampling circuit 2310 provides an electrogram of an intracardiac signal. In some examples, the cardiac signal sensing circuit 2305 includes an external or surface electrode and the sampling circuit provides an ECG of an externally sensed cardiac signal.

The device 2300 also includes a therapy circuit 2315. The therapy circuit 2315 provides one or more of high-energy cardioversion shock therapy, high-energy defibrillation shock therapy, and anti-tachycardia pacing (ATP) to the heart of the subject. In some examples, the device 2300 is implantable (e.g., an ICD) and the therapy circuit 2315 delivers the therapy using an implantable electrode. In some examples, the device 2300 is external (e.g., WCD or AED) and the therapy circuit 2315 delivers the therapy using a surface or external electrode.

A controller 2320 is communicatively coupled to the sampling circuit 2310 and the therapy circuit 2315. The communicative coupling allows the controller 2320 to communicate electrical signals with the sampling circuit 2310 and therapy circuit 2315 even though there may be intervening circuitry between the controller 2320 and the sampling circuit 2310 and therapy circuit 2315. In some examples, the controller 2320 includes a processor such as a microprocessor, a digital signal processor, application specific integrated circuit (ASIC), microprocessor, or other type of processor, interpreting or executing instructions in software or firmware. The controller 2320 includes modules to perform the functions described. Modules can be software, hardware, firmware or any combination thereof. Multiple functions can be performed in one or more modules as desired.

The controller 2320 includes a detection module 2325 configured to detect tachyarrhythmia using the cardiac signal. In some examples, the device 2300 includes an electrode that is part of a rate sensing channel (e.g., one or both of electrodes 135, 140 in FIG. 1). The detection module 2325 first detects a tachyarrhythmia by using heart rate or depolarization rate of the subject.

Heart rate based tachyarrhythmia detection may include a measure of heart rate or rate interval. In some examples, the detection module 2325 detects tachyarrhythmia when heart rate determined from heart beats sensed in the cardiac signal exceeds a tachyarrhythmia detection rate threshold or satisfies an interval threshold. In some examples, the detection module 2325 compares heart rate or depolarization interval to one or more of a VT-1 zone, a VT zone, or a VF zone to detect and categorize a detected arrhythmia as slow VT, VT, or VF respectively.

Heart rate based tachyarrhythmia detection may further include one or both of measures of rate stability, and the ratio of ventricular rate to atrial rate (V:A). One or more of such measures can be compared to corresponding threshold values programmed into the device, such as to discriminate between the various types of tachyarrhythmia. Heart rate based tachyarrhythmia detection can also include detection of gradual or sudden tachyarrhythmia onset.

In some examples, the detection module 2325 uses a combination of heart rate based tachyarrhythmia detection with morphology based tachyarrhythmia classification. The morphology-based method typically compares the morphological shape of a cardiac depolarization to a morphology template to classify a heart beat or heart rhythm. In the comparison, a correlation value can be determined (e.g., a feature correlation coefficient (FCC)) that can provide an indication of a degree of similarity between the shape of a depolarization being examined and the shape of the template to which it is compared. The correlation value can be compared to a correlation threshold value (e.g., $FCC_{th}$), such as to classify the rhythm as VT or SVT (e.g., ST, atrial fibrillation (AF), atrial flutter (AFL), or atrial tachyarrhythmia).

The controller 2320 also includes a signal analysis module 2330 to establish SPs in the sensed and sampled cardiac signal. As explained previously, an SP corresponds to a time of occurrence of a turn encountered in the sensed cardiac signal. The signal analysis module 2330 estimates heart rate during the detected arrhythmia using the established SPs.

According to some examples, the signal analysis module 2330 determines rate by performing the SP1 autocorrelation in the SP domain as described previously in regard to FIGS. 9, 11, 13, and 15. The signal analysis module 2330 calculates the number of SPs per heart beat from an SP shift that produces a peak in the autocorrelation and estimates heart rate using the number of SPs per heart beat and using the number of SPs per second or per minute. In some examples, the signal analysis module 2330 filters the SP1 autocorrelation, such as described previously in regard to FIG. 10, and estimates rate by calculating the number of SPs per heart beat from an SP shift that produces a peak in the filtered autocorrelation.

In some examples, the signal analysis module 2330 performs autocorrelation of the SPs in an SP domain and performs a second autocorrelation of the SP autocorrelation (e.g., the SP2 autocorrelation described above in regard to FIGS. 11, 13, and 15). The signal analysis module 2330 then calculates the number of SPs per heart beat from an SP shift that produces a peak in the second autocorrelation and estimates heart rate using the number of SPs per heart beat.

The signal analysis module 2330 may also provide an indication of whether noise is present in the cardiac signal using the SPs. According to some examples, the signal analysis module 2330 determines a probability of noise in the cardiac signal using the SPs. As described above in regard to FIGS. 19A, 19B, and 20, in some examples, the signal analysis module 2330 identifies a number of approximate SP pairs in the cardiac signal, and calculates the probability of noise in the cardiac signal using the number of approximate SP pairs or the number of SPs that satisfy a pair-matching criterion. In some examples, the signal analysis module 2330 determines the number of SPs per second and calculates the probability of noise using the number of SPs per second, such as by using the equation for the PR[Noise] described previously.

Based on the calculated probability of noise, the signal analysis module 2330 may generate an indication of noise to the controller, such as when the calculated probability exceeds a specified probability threshold.

The controller 2320 selects an appropriate therapy for delivery to the subject by the therapy circuit 2315 in response to the tachyarrhythmia detection by the detection module 2325. For instance, if the detection module 2325 determines that the rate or interval is stable (e.g., monomorphic VT), the controller 2320 may attempt to first treat the tachyarrhythmia using ATP. If the rate or interval is unstable (e.g., polymorphic VT), the controller 2320 may bypass treatment with ATP and directly deliver shock therapy.

Once the therapy is selected, the controller 2320 may then modify the selected therapy according to the SP-based heart rate estimation and the noise indication. In some examples, the controller 2320 changes the therapy from a more aggressive therapy to a less aggressive therapy according to the SP-based rate estimate and noise estimate. Changing therapy from an aggressive therapy type to a less aggressive includes changing from defibrillation shock therapy to cardioversion shock therapy, changing from defibrillation therapy to ATP, and changing from cardioversion shock therapy to ATP.

In an illustrative example, the detection module 2325 may detect a heart rate or interval that is within the VF detection zone, such as by detecting heart beats in a cardiac signal sensed using a rate channel. In response to the detected rate or interval, the controller 2320 may select to deliver defibrillation therapy. If the signal analysis module 2330 a) estimates that the SP-based rate is within a lowest tachyarrhythmia detection rate zone (e.g., a VT−1 rate zone), and b) assesses that a probability of noise is above a noise probability threshold value, the controller 2320 may change the selected therapy type to ATP.

In some examples, the controller 2320 selects to deliver a less aggressive type of therapy when the probability of noise is above the noise probability threshold value and the heart rate estimated using the SPs is within or below the lowest tachyarrhythmia detection rate zone. In some examples, the controller 2320 selects to deliver a less aggressive therapy when the probability of noise is above the noise probability threshold value and the heart rate estimated using the SPs is lower than a specified fraction (e.g., 50%) of the rate detection method used by the detection module 2325 (e.g., rate channel detection).

According to some examples, once therapy is detected, the controller 2320 may decide to change the timeframe of the therapy based on the noise assessment and the rate estimate provided by the signal analysis module 2330. In certain examples, the controller 2320 withholds delivery of the selected therapy when the noise assessment indicates that a probability of noise is above a noise probability threshold value and the SP-based estimated heart rate is lower than the lowest tachyarrhythmia detection rate zone.

In some examples, the detection module 2325 detects tachyarrhythmia when the heart rate determined from heart beats sensed in the cardiac signal (e.g., using a rate channel) exceeds a tachyarrhythmia detection rate threshold or interval threshold. The controller 2320 withholds delivery of the selected therapy when the noise assessment indicates that the calculated probability of noise is above a noise probability threshold value and the rate estimated using the SPs differs from the heart rate determined from the sensed cardiac signal by the detection module 2325 by more than a threshold difference value. In some examples, the controller 2320 does not modify the selected therapy if the signal analysis module 2330 can not determine either an SP-based rate estimate or the noise estimate.

Figure 24:
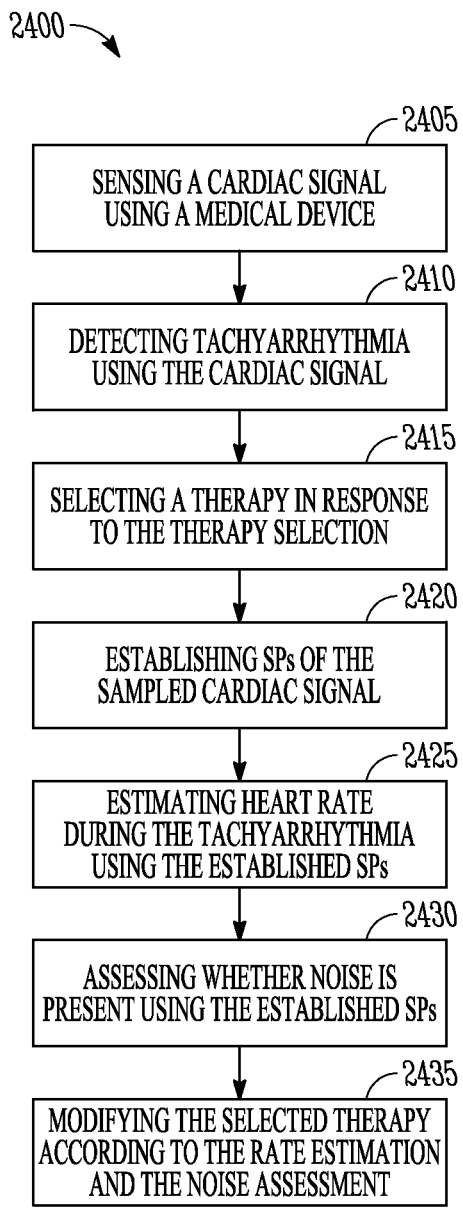
FIG. 24 shows a flow diagram of an example of a method for providing tachyarrhythmia therapy to a subject.

FIG. 24 shows a flow diagram of an example of a method 2400 for providing tachyarrhythmia therapy to a subject. At block 2405, a cardiac signal is sensed and sampled using a medical device that delivers at least one of high-energy cardioversion, high-energy defibrillation shock therapy, or anti-tachycardia pacing (ATP). In some examples, the cardiac signal is sensed using a rate channel. At block 2410, tachyarrhythmia is detected using the cardiac signal.

In response to the tachyarrhythmia detection, at block 2415, a therapy is selected for delivery by the medical device, and at block 2420 SPs of the sampled cardiac signal are established. Each SP corresponds to a turn encountered in the cardiac signal.

At block 2425, heart rate is estimated during the tachyarrhythmia using the SPs. The estimation is made using any of the SP-based methods described. At block 2430, whether noise is present in the cardiac signal is assessed using the SPs.

At block 2435, the selected therapy is modified according to the rate estimation and the noise assessment. In some examples, therapy is modified by being withheld for a predetermined period of time. This allows time for the arrhythmia to resolve itself on its own. In certain examples, therapy is modified by being changed to a less aggressive therapy.

According to some examples, therapy is withheld if the noise estimate exceeds a threshold value (e.g., a calculated noise probability greater than 25%) and the SP-based rate estimate is lower than a specified threshold value (e.g., 100 bpm). In certain examples, therapy is withheld if the noise estimate exceeds a threshold value and the SP-based rate estimate lower than the lowest programmed rate threshold used by the medical device to detect arrhythmia (e.g., lower than VT−1, VT, or VF programmed rate zones for a three-zone device, or less than VT or VF programmed rate zones for a two-zone device).

In some examples, therapy is withheld if the noise estimate exceeds a threshold value and the SP-based rate estimate is lower than a specified fraction (e.g., <50%) of the non-SP-based device rate estimation method. In some examples, therapy is withheld if the noise estimate exceeds a threshold value and the SP-based rate estimate is less than the specified fraction of the non-SP-based device rate estimation method, or the SP-based rate is less than a specified rate threshold (e.g., 140 bpm) and is below the VT specified rate.

In some examples, a selected therapy is modified to a less-aggressive therapy type if the noise estimate exceeds a specified threshold value and SP-based rate estimate is in the VT−1 detection zone.

The concurrent consideration of the SP-based rate estimate and the SP-based noise estimate provide further discrimination of device detected tachyarrhythmia. This enhanced discrimination reduces inappropriately delivered shock therapy due to signal noise; particularly due to signal noise in the ventricular chambers that a medical device may interpret to be an arrhythmia.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile tangible computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   a cardiac signal sensing circuit configured to provide a sensed electrical cardiac signal representative of cardiac activity of a subject;
   a sampling circuit coupled to the cardiac signal sensing circuit;
   a therapy circuit, configured to provide one or more of high-energy cardioversion shock therapy, high-energy defibrillation shock therapy, and anti-tachycardia pacing (ATP) to the heart; and
   a controller communicatively coupled to the sampling circuit and the therapy circuit, wherein the controller includes:
      a detection module configured to detect tachyarrhythmia using the cardiac signal; and
      a signal analysis module configured to:
         establish significant points (SPs) of the sampled cardiac signal, wherein an SP corresponds to a time of occurrence of a turn encountered in the cardiac signal;
         perform autocorrelation of the SPs in an SP domain;
         perform a second autocorrelation of the SP autocorrelation;
         calculate a number of SPs per heart beat from an SP shift that produces a peak in the second autocorrelation; and
         estimate heart rate during the tachyarrhythmia using the number of SPs per heart beat; and
         determine a likelihood of the presence of noise in the cardiac signal using the SPs,
      and wherein the controller is configured to select a therapy for delivery by the therapy circuit in response to the tachyarrhythmia detection and to modify the selected therapy according to the heart rate estimation and the determined likelihood of noise.

2. The apparatus of claim 1, wherein the signal analysis module is configured to determine a probability of noise in the cardiac signal using the SPs.

3. The apparatus of claim 2, wherein the signal analysis module is configured to:
   identify a number of approximate SP pairs in the cardiac signal, wherein an approximate SP pair includes two SPs that satisfy a specified matching criterion;
   calculate the probability of noise in the cardiac signal using the number of approximate SP pairs; and
   determine the likelihood of noise according to the calculated noise probability.

4. The apparatus of claim 2, wherein the signal analysis module is configured to:
   determine a number of SPs per second in the cardiac signal;
   calculate the probability of noise in the cardiac signal using the number of SPs per second; and
   determine the likelihood of noise according to the calculated noise probability.

5. The apparatus of claim 1, wherein the signal analysis module is configured to:
   filter the SP autocorrelation; and
   calculate a number of SPs per heart beat from an SP shift that produces a peak in the filtered autocorrelation.

6. The apparatus of claim 1, wherein the controller is configured to change a selected therapy type to a less aggressive therapy type when the estimated heart rate is within a lowest tachyarrhythmia detection rate zone and a noise assessment indicates that a probability of noise is above a noise probability threshold value.

7. The apparatus of claim 1, wherein the controller is configured to withhold delivery of the selected therapy when a noise assessment indicates that a probability of noise is above a noise probability threshold value and the estimated heart rate is lower than a lowest tachyarrhythmia detection rate zone.

8. The apparatus of claim 1,
   wherein the detection module is configured to detect tachyarrhythmia when heart rate determined from heart beats sensed in the cardiac signal exceeds a tachyarrhythmia detection rate threshold or interval threshold; and wherein the controller is configured to withhold delivery of the selected therapy when a noise assessment indicates that a probability of noise is above a noise probability threshold value and the heart rate estimated using the SPs differs by more than a specified threshold value from the heart rate determined from the sensed cardiac signal.

9. The apparatus of claim 1,
wherein the detection module is configured to detect tachyarrhythmia when heart rate determined from heart beats sensed in the cardiac signal exceeds a tachyarrhythmia detection rate threshold or interval threshold; and wherein the controller is configured to deliver a type of therapy less aggressive than the selected therapy when a noise assessment indicates that a probability of noise is above a noise probability threshold value, and the heart rate estimated using the SPs is within or below a lowest tachyarrhythmia detection rate zone.

10. A method comprising:
sampling a sensed cardiac signal using a medical device that delivers at least one of high-energy cardioversion, high-energy defibrillation shock therapy, and anti-tachycardia pacing (ATP), wherein the sensed cardiac signal is an electrical signal representative of cardiac activity of a subject;

detecting tachyarrhythmia using the cardiac signal; and, in response to the tachyarrhythmia detection:
selecting a therapy for delivery by the medical device;
establishing significant points (SPs) of the sampled cardiac signal, wherein an SP corresponds to a turn encountered in the cardiac signal;
estimating heart rate during the tachyarrhythmia using the SPs, wherein estimating heart rate using the SPs includes:
performing autocorrelation in an SP domain;
performing a second autocorrelation of the SP autocorrelation; and
calculating a number of SPs per heart beat from an SP shift that produces a peak in the second autocorrelation;
determining a likelihood of a presence of noise in the cardiac signal using the SPs; and
modifying the selected therapy according to the rate estimation and the determined likelihood of noise.

11. The method of claim 10, wherein determining a likelihood of a presence of noise includes determining a probability of noise in the cardiac signal using the SPs.

12. The method of claim 11, wherein determining a probability of noise includes identifying a number of approximate SP pairs in the cardiac signal and calculating the probability of noise in the cardiac signal using the number of approximate SP pairs, wherein an approximate SP pair includes two SPs that satisfy a specified matching criterion.

13. The method of claim 11, wherein determining a probability of noise includes calculating the probability of noise in the cardiac signal using a number of SPs per second in the cardiac signal.

14. The method of claim 10, wherein estimating heart rate using the SPs includes:
performing autocorrelation in an SP domain;
filtering the SP autocorrelation; and
calculating a number of SPs per heart beat from an SP shift that produces a peak in the filtered autocorrelation.

15. The method of claim 11, wherein modifying the selected therapy includes changing a selected therapy type to a less aggressive therapy type when the estimated heart rate is within a lowest tachyarrhythmia detection rate zone and the probability of noise is above a noise probability threshold value.

16. The method of claim 11, wherein modifying the selected therapy includes withholding delivery of the selected therapy when the probability of noise is above a noise probability threshold value and the estimated heart rate is lower than a lowest tachyarrhythmia detection rate zone.

17. The method of claim 11,
wherein detecting tachyarrhythmia using the cardiac signal includes detecting tachyarrhythmia when heart rate determined from the cardiac signal exceeds a tachyarrhythmia detection rate threshold or interval threshold; and
wherein modifying the selected therapy includes withholding delivery of the selected therapy when the probability of noise is above a noise probability threshold value and the heart rate estimated using the SPs differs by more than a specified threshold value from the heart rate determined from the sensed cardiac signal.

18. The method of claim 11,
wherein detecting tachyarrhythmia using the cardiac signal includes detecting tachyarrhythmia when heart rate determined from the cardiac signal exceeds a tachyarrhythmia detection rate threshold or interval threshold; and
wherein modifying the selected therapy includes withholding delivery of the selected therapy when the probability of noise is above a noise probability threshold value, the heart rate estimated using the SPs differs by less than a specified threshold value from the heart rate determined from the sensed cardiac signal, and the heart rate estimated using the SPs is less than a lowest tachyarrhythmia detection rate zone.

* * * * *